US006815205B2

(12) United States Patent
Lin et al.

(10) Patent No.: US 6,815,205 B2
(45) Date of Patent: Nov. 9, 2004

(54) AUXINIC ANALOGUES OF INDOLE-3-ACETIC ACID

(75) Inventors: Jhy-Jhu Lin, Potomac, MD (US); Jianqing Lan, Germantown, MD (US); Nacyra Assad-Garcia, Gaithersburg, MD (US)

(73) Assignee: Invitrogen Corporation, Carlsbad, CA (US)

( * ) Notice: Subject to any disclaimer, the term of this patent is extended or adjusted under 35 U.S.C. 154(b) by 96 days.

(21) Appl. No.: 09/778,132

(22) Filed: Feb. 6, 2001

(65) Prior Publication Data

US 2003/0087762 A1 May 8, 2003

Related U.S. Application Data

(63) Continuation of application No. 08/758,416, filed on Nov. 29, 1996, which is a continuation-in-part of application No. 08/430,209, filed on Apr. 27, 1995, now Pat. No. 5,674,731.
(60) Provisional application No. 60/007,770, filed on Nov. 30, 1995.

(51) Int. Cl.$^7$ ................................................. C12N 5/00
(52) U.S. Cl. ...................... 435/410; 435/420; 435/421; 501/136; 501/138; 501/189; 501/284; 47/58.1
(58) Field of Search ................................. 435/410, 421, 435/420; 504/136, 138, 189, 284; 47/58.1

(56) References Cited

U.S. PATENT DOCUMENTS

| | | | |
|---|---|---|---|
| 3,000,888 A | 9/1961 | Biekert ........................ | 504/136 |
| 4,297,125 A | 10/1981 | Haissig et al. .................. | 71/77 |
| 4,411,684 A | 10/1983 | Boyles et al. ................ | 504/138 |
| 4,455,162 A | 6/1984 | Welebir ........................ | 504/121 |
| 4,637,828 A | 1/1987 | Schulze et al. ................. | 71/76 |
| 4,806,483 A | 2/1989 | Wang ..................... | 435/240.49 |
| 5,004,863 A | 4/1991 | Umbeck ...................... | 800/205 |
| 5,134,074 A | 7/1992 | Gordon et al. ........... | 435/240.4 |
| 5,188,655 A | 2/1993 | Jones et al. .................. | 504/136 |
| 5,674,731 A | 10/1997 | Lin et al. .................. | 435/240.4 |
| 5,994,135 A | 11/1999 | Lin et al. .................... | 435/421 |
| 6,271,032 B1 | 8/2001 | Lin et al. .................... | 435/424 |
| 6,361,999 B1 * | 3/2002 | Lin et al. | |

FOREIGN PATENT DOCUMENTS

| | | | |
|---|---|---|---|
| JP | 02265473 | 10/1990 | |
| WO | WO 96/34089 | 10/1996 | ............ C12N/5/00 |

OTHER PUBLICATIONS

Abdullah et al. (1986) "Efficient Plant Regeneration from Rice Protoplasts Through Somatic Embryogenesis," *Bio/Technology* 6:1087–1090.

Aberg (1978) "Plant growth regulators," *Swedish J. Agric. Res.* 8(3):133–138.

Altamura et al. (1992) "The role of hormones on morphogenesis of thin layer explants from normal and transgenic tobacco plants," *Physiologia Plantarum* 84:555–560.

Baldi, B.G. et al. (1984) "Synthesis of $C^{14}$–Labeled Halogen Substituted Indole–3–acetic Acids," *J. Labelled Compounds and Radiopharmaceuticals* XII(3):279–285.

Barton et al. (1983) "Regeneration of Intact Tobacco Plants Containing Full Length Copies of Genetically Engineered T–DNA, and Transmission of T–DNA to R1 Progeny," *Cell* 32:1033.

Böttger, M. et al. (1978) "Growth of Avena Coleoptiles and pH Drop of Protoplast Suspensions Induced by Chlorinated Indoleacetic Acids," *Planta* 140:89–92.

Burns, J.A. and Schwarz, O.J. (Feb. 1996) "Bacterial stimulation of adventitious rooting on in vitro cultured slash pine (*Pinus ellitiotti* Englem.) Seedling explants," *Plant Cell Reports* 15:405–408.

Chang, S.S. et al. (Apr. 1994) "Stable genetic transformation of *Arabidopsis thaliana* by Agrobacterium inoculation in planta," *The Plant Journal* 5(4):551–558.

Chee, P. P. (Oct. 1995) "Stimulation of adventitious rooting of *Taxus* species by thiamine," *Plant Cell Reports* 14:753–757.

Chemical Abstracts vol. 100, No. 19, May 7, 1984, Abstract No. 156493, Nissan Chemical Industries Ltd. JP58 189162, Abstract.

Chemical Abstracts vol. 61, No. 2, Jul. 20, 1964, Abstract.

Chilton, M–D et al. (1974) "*Agrobacterium tumefaciens* DNA and PS8 Bacteriophase DNA Not Detected in Crown Gall Tumors," *Proc. Nat. Acad. Sci. USA* 71(9):3672–3676.

Cleland, R.E. (1995) "D1. Auxin and Cell Elongation," in *Plant Hormones*, P.J. Davies (ed.) Kluwer Academic Publishers, Netherlands, pp. 214–227.

Davies, P.J. (1995) "A1. The Plant Hormones: Their Nature, Occurrence, and Functions," in *Plant Hormones. Physiology, Biochemistry and Molecular Biology*, $2^{nd}$ Ed., P.J. Davies (ed.) Kluwer Academic Publishers, Norwell, MA, pp. 1–12.

Dekeyser, R.A. et al. (1990) "Transient Gene Expression in Intact and Organized Rice Tissues," *The Plant Cell* 2:591–602.

(List continued on next page.)

Primary Examiner—Leon B. Lankford, Jr.
(74) *Attorney, Agent, or Firm*—Greenlee, Winner and Sullivan, P.C.

(57) ABSTRACT

The present invention provides compounds and compositions capable of stimulating plant growth, regeneration of plant cells and tissues, and transformation of plant cells and tissues, comprising mono- and multi-substituted auxinic analogues of indole-3-acetic acid (IAA) comprising substituent groups such as halo-, alkyl-, alkoxy-, acyl-, acylamido- and acyloxy-groups. The invention relates to a method of using such mono- and multi-substituted auxinic analogues of IAA to affect growth, regeneration or transformation in monocotyledonous and dicotyledonous plants, as well as in transgenic plant tissues. The invention also contemplates the use of these auxinic IAA analogues in the presence of other plant growth regulators, such as cytokinin, etc., to enhance plant growth.

21 Claims, 13 Drawing Sheets

OTHER PUBLICATIONS

Engvild, K.C. (1977) "Preparation of Chlorinated 3–Indolylacetic Acids," *Acta Chem. Scand.* B31:338–339.

Engvild, K.C. (1978) "Substituted Indoleacetic Acids Tested in Tissue Cultures," *Physiol. Plant* 44:345–346.

Evans, M.L., "Functions of Hormones at the Cellular Level of Organization," Hormone Regulation of Development II. Encyclopedia of Plant Physiology (T.K. Scott, ed.) Springer Verlag, Heidelberg, pp. 23–78.

Ferdinandi, E.S. et al. (1978) "Synthesis of [$^{14}$C]Labelled Pyranol[3,4–b]–and Thiopyranol [3,4–b]–Indoles, and Indenol[2,1–c]Pyran Derivatives," *J. Labelled Compounds and Radiopharmaceuticals* 14(3):411–425.

Fox, S.W. and Bullock, M.W. (1951) "Synthesis of Indole–3–acetic Acids and 2–Carboxyindole–3–acetic Acids with Substituents in the Benzene Ring," J. Am. Chem. Soc. 73:2756–2759.

Hatano, T. et al. (1987) "5,6–Dichloroindole–3–acetic acid as a potent auxin: its synthesis and biological activity," Experientia 43:1237–1239.

Hiei, Y. et al. (Aug. 1994) "Efficient transformation of rice (*Oryza sativa* L.) mediated by *Agrobacterium* and sequence analysis of the boundaries of the T–DNA," *The Plant Journal* 6:001–011.

Hoffman, O.L. et al. (1952) "Auxin–Like Activity of Systematically Substituted Indoleacetic Acid," *J. Biol. Chem.* 196:437–441.

Hooykaas–Van Slogteren, G.M.S. et al. (1984) "Expression of Ti plasmid genes in monocotyledonous plants infected with *Agrobacterium tumefaciens*," *Nature* 311:763–764.

Ilic, N. et al. (1991) "Synthesis of 5–Alkylindole–3–acetic Acids for Use as Plant Hormone Analogues," Croatica Chemica Acta. 64(1):79–88.

Jefferson, R.A. et al. (1987) "GUS fusions: β–glucuronidase as a sensitive and versatile gene fusion marker in higher plants," *EMBO J.* 6(13):3901–3907.

Katayama, M. et al. (1988) "Localization of 4–Chloroindole–3–acetic Acid in Seeds of Pisum sativum and Its Absence from All Other Organs," *Plant Cell Physiol.* 29(5):889–891.

Katekar, G.F. and Geissler, A.E. (1982) "Auxins II: The Effect of Chlorinated Indoylacetic Acids on Pea Stems," *Phytochemistry* 21:(2):257–260.

Katekar, G.F. and Geissler, A.E. (1983) "Structure–Activity Differences Between Indoeacetic Acid Auxins on Pea and Wheat," *Phytochemistry* 22(1):27–31.

Lin, J. et al., "Effects of Agrobacterium Cell Concentration on the Transformation Efficiency of Tobacco and *Arabidopsis Thaliana*," *Focus* 16(3):72–77.

Lutz et al. (Sep. 1996) "FT–IR spectroscopic study of the phytohormone auxin (indol–3–ylacetic acid, IAA) and its n–alkylated and monohalogenated derivatives," *J. Molecular Structure* 382(3):177–185.

Marumo et al. (1973) "Biological Activity of 4–chlorindolyl 3–acetic," Proceed. 8$^{th}$ Int. Congr. Plant Growth Substances, Kirokawa Publ., Tokyo, pp. 419–428.

Masanori, S. (Feb. 1984) Patent Abstracts of Japan, vol. 008, No. 024 (C–208) publication No. 58189161A.

Mii, M. et al. (1992) "Shoot regeneration from spinach hypocotyl segments by short term treatment with 5,6–Dichloro–indole–3–acetic acid," *Plant Cell Reports* 11:58–61.

Mihaljevic, S. et al. (Apr. 1996) "Increase of root induction in *Pinus nigra* explants using agrobacteria," *Plant Cell Reports* 15:610–614.

Nilsson et al. (Oct. 1996) "Expression of the Agrobacterium Rhizogenes rolC gene in a deciduous forest tree alters growth and development and leads to stem fasciation," Plant Physiol. 112:493–502.

Porter, W.L. and Thimann, K.V. (1965) "Molecular Requirements for Auxin Action—I. Halogenated Indoles and Indoleacetic Acid," *Phytochemistry* 4:229–243.

Rasmussen, T. et al. (1995) "Auxin activity of brominated indoles from the marine sponge *Pseudosuberites hyalinus*," J. Mar. Biotechnol. 2(3):167–169.

Rawal, S.K. and Mehta, A.R. (1982) "Tissue Culture of Tobacco. II. Influence of IAA, Kinetin and Sucrose on Organogenesis in *Nicotiana tabacum* Callus Cultures," *Ind. J. Plant Physiol.* XXV(4):336–347.

Rescher et al. (Winter 1996) "In vitro binding affinites of 4–chloro–, 2–methyl–, and 4–ethylindoleacetic acid to auxin–binding protein 1 (ABP1) correlate with their growth–stimulating activities," *J. Plant Growth Regulation* 15(1):1–3.

Rhodes et al. (1988) "Generally Transformed Maize Plants from Protoplasts," *Science* 240:204–207.

Rhodes, C.A. et al. (1988) "Plant Regeneration from Protoplasts Isolated from Embryogenic Maize Cell Cultures," *Bio/Technology* 6:56–60.

Raineri, D.M. et al. (1990) "Agrobacterium–Mediated Transformation of Rice (*Oryza Sativa* L.)," *Bio/Technology* 8:33–38.

Reinecke et al. (Nov. 1995) "Effect of halogen substitution of indole–3–acetic acid on biological activity in pea fruit," Phytochemistry 40(5):1361–1366.

Saitou, T. et al. (1992) "Involvement of phytohormones in light–induced adventitious shoot formation of horseradish hair roots," Plant Science 86:161–166.

Schöpke, C. et al. (Jun. 1996) "Regeneration of transgenic cassava plants (*Manihot esculentia* Crantz) from microbombarded embryongenic suspension cultures," Nature Biotechnology 14:731–735.

Skoog, F. et al. (1967) "Cytokinins: Structure/Activity Relationships," *Phytochemistry* 6:1169–1192.

Skoog, F. and Tsui, C. (1951) "Growth Substances and the Formation of Buds in Plant Tissues," *Plant Growth Substances*, University of Wisconsin Press, Madison, WI, p. 263.

Skoog, F. and Miller, C.O. (1957) "Chemical Regulation of Growth and Organ Formation in Plant Tissues Cultured In Vitro," *Symposia Society for Experimental Biology* 11:188–231.

Thomson et al. (1988) "The response of stomata to ring–substituted indolylacetic acids," New Phytol. 110:511–515.

Ulvskov et al. (1992), "Immunoaffinity purification using monoclonal antibodies for the isolation of indole auxins from elongation zones of epicotyls of red–light–grown Alaska peas," Planta 188(2):182–189.

Vanderhoef, L.N. et al. (1977) "Comparison of Auxin–induced and Acid–induced Elongation in Soybean Hypocotyl," Plant Physiol. 59:1004–1007.

Vasil, I. K. (1988) "Progress in the Regeneration and Genetic Manipulation of Cereal Crops," *Bio/Technology* 6:397–402.

Vasil, I.K. and Vasil, V., (1994) "In vitro Culture of Cereals and Grasses," Plant Cell and Tissue Culture, pp. 293–312.

Vetter, J. (1974) "The Auxin–induced Growth of Tobacco Callus Tissue," *Biochem. Physiol. Pfllanzen* (BPP) 165:114–118.

Wang, Y–C et al. (1988) "Transient expression of foreign genes in rice, wheat and soybean cells following particle bombardment," *Plant Mol. Biol.* 11:433–439.

Winans, S.C. et al. (1988) "Transcriptional Regulation of the virA and virG Genes of *Agrobacterium tumefaciens*," *J. Bacteriology* 170(9):4047–4054.

* cited by examiner

Halogenated IAA Analogues 2-iodo-IAA 2-bromo-IAA 2-fluoro-IAA 4-iodo-IAA 4-bromo-IAA 4-fluoro-IAA 5-iodo-IAA 5-bromo-IAA 5-fluoro-IAA 6-iodo-IAA 6-bromo-IAA 6-fluoro-IAA 7-iodo-IAA 7-bromo-IAA 7-fluoro-IAA 4-Alkyl-IAA Auxinic Analogues 4-methyl-IAA 4-ethyl-IAA 4-propyl-IAA 4-isopropyl-IAA 4-butyl-IAA 4-sec-butyl-IAA 4-isobutyl-IAA 4-tert-butyl-IAA 4-cyclobutyl-IAA 4-Alkoxy-IAA Auxinic Analogues 4-methoxy-IAA 4-ethoxy-IAA 4-propoxy-IAA 4-isopropoxy-IAA 4-butoxy-IAA 4-sec-butoxy-IAA 4-isobutoxy-IAA 4-tert-butoxy-IAA 4-cyclobutoxy-IAA 4-Acyl-IAA Auxinic Analogues 4-acetyl-IAA 4-propionyl-IAA 4-butyryl-IAA 4-isobutyryl-IAA 4-valeryl-IAA 4-sec-valeryl-IAA 4-iso-valeryl-IAA 4-tert-valeryl-IAA 4-cyclovaleryl-IAA

AUXINIC ANALOGUES OF INDOLE-3-ACETIC ACID

CROSS-REFERENCE TO RELATED APPLICATIONS

This application is a continuation of U.S. patent application Ser. No. 08/758,416, filed Nov. 29, 1996 which is a continuation-in-part of provisional application No. 60/007,770 filed Nov. 30, 1995, and copending application Ser. No. 08/430,209 filed Apr. 27, 1995 now U.S. Pat. No. 5,674,731, all of which are incorporated herein by reference in their entirety.

FIELD OF THE INVENTION

This invention relates to the use of an indole-3-acetic acid (IAA) analogue as a plant hormone stimulatory to plant growth, to regeneration of plant cells and tissues, and to transformation of plant cells. It particularly relates to the use of mono- and multi-substituted IAA molecules. The invention also relates to compositions comprising IAA analogues of the invention.

BACKGROUND OF THE INVENTION

Plant growth is affected by a variety of physical and chemical factors. Physical factors include available light, day length, moisture and temperature. Chemical factors include minerals, nitrates, cofactors, nutrient substances and plant growth regulators or hormones, for example, auxins, cytokinins and gibberellins.

Indole-3-acetic acid (IAA) is a naturally-occurring plant growth hormone identified in plants. IAA has been shown to be directly responsible for the increase in growth in plants in vivo and in vitro. The characteristics influenced by IAA include cell elongation, internodal distance (height), leaf surface area and crop yield. IAA and other compounds exhibiting hormonal regulatory activity similar to that of IAA are included in a class of plant regulators called "auxins."

Preparations based on cytokinins, such as 6-furfurylamino purine (kinetin) and 6-benzylamino purine (BAP), are also known to be growth stimulators. However, cytokinin-based preparations are most effective in combination with auxins. While the mechanism by which cytokinins affect the growth cycle of plants is far from being understood, it is apparent that they affect leaf growth and prevent aging in certain plants.

It is a general objective in the field to successfully engineer and regenerate plants of major crop varieties using methods such as tissue culture and genetic engineering. Major crop varieties of particular interest in this regard are agricultural crops such as maize, wheat, rice, soybeans and cotton.

To regenerate plants, in vitro culture techniques have been established. (Reinert, J., and Bajaj, Y. P. S., eds. (1977) *Plant Cell, Tissue and Organ Culture*, Berlin: Springer; Simmonds, N. W. (1979) *Principles of Crop Improvement*, London: Longman; Vasil, I. K., Ahuja, M. K. and Vasil, V. (1979) "Plant tissue cultures in genetics and plant breeding," *Adv. Genet.* 20:127–215.) Specific in vitro culture techniques to regenerate plants include embryo culturing shoot tip culturing and callus, cell and protoplast culturing. Embryo culturing has been shown to be important in making difficult interspecies crosses, while shoot-tip culturing is important in rapid clonal multiplication, development of virus-free clones and genetic resource conservation work. Callus, cell, and protoplast cultures have been shown to be important for cultures in which organization is lost but can be recovered.

Plant genetic engineering techniques have also been established. These techniques include gene transfer by transformation or by protoplast fusion. In gene transfer, the steps involved are: (a) identification of a specific gene; (b) isolation and cloning of the gene; (c) transfer of the gene to recipient plant host cells: (d) integration, transcription and translation of the DNA in the recipient cells; and (e) multiplication and use of the transgenic plant (T. Kosuge, C. P. Meredith and A. Hollaender, eds (1983) *Genetic Engineering of Plants*, 26:5–25; Rogers et al. (1988) *Methods for Plant Molecular Biology* Academic Press, Inc., San Diego, Calif.). In protoplast fusion, plant cell protoplasts are fused by standard chemical (e.g., PEG) or electroporation techniques. After regeneration of the fused cells, interspecies amphidiploids have been obtained. The technique may provide desired amphidiploids which cannot be made by conventional means, and presents possibilities for somatic recombination by some variant of it. The foregoing techniques are widely in use (Chaleff, R. S. (1981) *Genetics of Higher Plants, Applications of Cell Culture*, Cambridge: Cambridge University Press), and newly inserted foreign genes have been shown to be stably maintained during plant regeneration and are transmitted to progeny as typical Mendelian traits (Horsch et al. (1984) Science 223:496, and DeBlock et al. (1984) EMBO 3:1681). These foreign genes retain their normal tissue specific and developmental expression patterns.

The *Agrobacterium tumefaciens*-mediated transformation system has proved to be efficient for many dicotyledonous plant species. For example, Barton et al. (1983, Cell 32:1033) reported the transformation and regeneration of tobacco plants, and Chang et al. (1994, Planta 5:551–558) described stable genetic transformation of *Arabidopsis thaliana*.

The *Agrobacterium* method for gene transfer was also applied to monocotyledonous plants, e.g., in plants in the Liliaceae and Amaryllidaceae families (Hooykaas-Van Slogteren et al., 1984, Nature 311:763–764) and in *Dioscorea bulbifera* (yam) (Schafer et al., 1987, Nature 327:529–532); however, this method did not appear to be efficient for the transformation of graminaceous monocots, which include such food crops as wheat, rice and corn.

Transformation of food crops was obtained with alternative methods, e.g., by polyethylene glycol (PEG)-facilitated DNA uptake (Uchimiya et al. (1986) Mol. Gen. Genet. 204:204–207) and electroporation (Fromm et al. (1986) Nature 319:791–793), both of which used protoplasts as transfer targets. Monocot and dicot tissues may be transformed by bombardment of tissues by DNA-coated particles (Wang et al. (1988) Plant Mol. Biol. 11:433–439; Wu, in *Plant Biotechnology* (1989), Kung and Arntzen, Eds., Butterworth Publishers, Stoneham, Mass.). Regeneration was described in rice (Abdullah et al. (1986) Bio/Technology 4:1087–1090) and maize (Rhodes et al. (1988) Bio/Technology 6:56–60 and (1988) Science 240:204–207).

Thus, although regeneration and transformation protocols have been established, there remains a need to stimulate regeneration and transformation of monocotyledonous and dicotyledonous plants. Indeed, some plants have been difficult to regenerate and transform [Vasil and Vasil (1994) in *Plant Cell and Tissue Culture* (Vasil and Thorpe, eds.), Kluwer Academic Publishers, Dordrech, Netherlands; Chee (1995) Plant Cell Reports 14:753–757; Burns and Schwartz (1996) Plant Cell Reports 15:405–408; Mihaljevic et al. (1996) Plant Cell Reports 15:610–614; Schopke et al. (1996) Nature Biotechnology 14:731). Moreover, there is a need to stimulate growth of the plants, particularly after transformation and regeneration.

SUMMARY OF THE INVENTION

The present invention satisfies these needs by providing compounds and compositions which stimulate plant growth, regeneration of plant cells and tissues, and transformation of plant cells and tissues. The compounds of the invention comprise mono- or multi-substituted IAA (indole-3-acetic acid) or ester or salt derivatives thereof. The invention also provides compositions comprising one or more of these IAA analogues and, optionally, a carrier. The invention contemplates the use of such auxinic analogues to affect growth, regeneration and transformation in both monocotyledonous and dicotyledonous plants. In particular, the invention provides monosubstituted IAA analogues having a substituent group at the 2, 4, 5, 6 or 7 position of the IAA structure, wherein said substituents are halo- or alkyl-, alkoxy-, acyl-, acylamido- and acyloxy-substituent groups having 1–10 carbon atoms. The invention also provides multi-substituted IAA analogues having two to five, same or different, substituent groups at different positions selected from positions 2, 4, 5, 6 or 7 of the IAA structure wherein said substituents are halo- or alkyl-, alkoxy-, acyl-, acylamido- and acyloxy-substituent groups having 1–10 carbon atoms.

The compositions of the invention may include, in addition to one or more of the mono- or multi-substituted compounds, one or more additional plant growth regulators. Such plant growth regulators include, for example, a cytokinin, a gibberellin, etc., in definite proportions for wide application to various plants. In specific embodiments, the invention is exemplified with compositions comprising mono- or multi-substituted IAA analogues having between one and five, same or different, substituent groups that are halo-, alkyl-, alkoxy-, acyl-, acylamido- or acyloxy-substituent groups at positions 2, 4, 5, 6 and/or 7 of the IAA structure, and a cytokinin to affect the growth of plants.

The invention further relates to media comprising the compounds and compositions of the invention. Such media comprise one or more IAA analogues and optionally an IAA analogue and optionally a plant growth regulator, e.g., cytokinin, to stimulate plant growth, to stimulate regeneration of plant cells and tissues, and to stimulate transformation of plant cells and tissues.

The invention also relates to a method of stimulating plant growth comprising (a) applying to a plant, plant cell or tissue an effective amount of the compound or composition of the invention and optionally, applying one or more additional plant growth regulators, for example, a cytokinin, a gibberellin, etc., and (b) incubating the plant cell or tissue under conditions sufficient to stimulate the regeneration of the plant cell or tissue.

The invention also provides a method for stimulating the regeneration of plant cells and/or tissues comprising (a) applying to a plant cell or tissue an effective amount of the compound or composition of the invention and applying one or more additional plant growth regulators, for example, a cytokinin, a gibberellin, etc., and (b) incubating the plant cell or tissue under conditions sufficient to stimulate the regeneration of the plant cell or tissue.

Also, the invention provides a method for stimulating the transformation of plant cells and/or tissues comprising (a) contacting the plant cell or tissue with a nucleic acid molecule (e.g., by transformation or protoplast fusion), (b) applying to the plant cell or tissue an effective amount of a compound or composition of the invention and, optionally, one or more additional plant growth regulators, for example, a cytokinin, a gibberellin, etc., and (c) incubating the plant cell or tissue under conditions sufficient to stimulate transformation of the plant cell or tissue with the nucleic acid molecule. The compounds and compositions of the invention also may be used to stimulate regeneration or growth of the transformed tissue or cells, thus providing a method to obtain a transgenic plant.

The invention also concerns a method of attentutating or alleviating environmental stress in a plant, plant cell or tissue comprising (a) contacting a plant, plant cell or tissue which has been exposed to an environmental stress (such as drought, excess temperature, diminished temperature, chemical toxicity [e.g., antibiotic, herbicides], pollution, excess light, and diminished light) with an effective amount of the compounds or compositions of the invention, and (b) incubating said plant, plant cell or tissue under conditions sufficient to attenuate or alleviate said stress.

DETAILED DESCRIPTION OF THE INVENTION

The following definitions are provided in order to provide clarity as to the intent or scope of their usage in the specification and claims.

Figure 1:
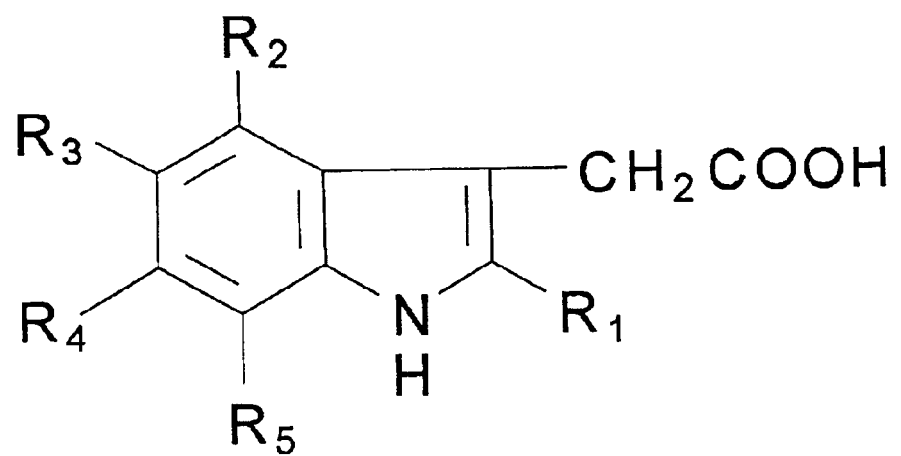
FIG. 1 presents the chemical structure of IAA where $R_1$–$R_5$ are hydrogen and the numbers (1)–(7) represent the numbering pattern for the IAA chemical structure.

The term indole-3-acetic acid or IAA as used herein refers to the chemical structure of FIG. 1 where $R_1$–$R_5$=hydrogen. This term refers not only to the free acid form but also to an amide, an ester or a salt form of IAA. Included in the meaning of IAA are, for example, such salt and ester derivatives as the sodium, potassium, ammonium, dimethylamine, ethanolamine, etc. salts and amides and the lower alkyl esters.

The term monosubstituted IAA as used herein refers to an IAA molecule of FIG. 1 where one or the $R_1$–$R_5$ groups represents a halo-, an alkyl-, an alkoxy-, an acyl-, an acylamido- or an acyloxy-substituent group at the 2, 4, 5, 6 or 7 position in the IAA chemical structure.

The term multi-substituted IAA as used herein refers to an IAA molecule of FIG. 1 where two or more of the $R_1$–$R_5$ groups represent the same or different halo-, alkyl-, alkoxy-, acyl-, acylamido- or acyloxy-substituent group in at least two of the positions corresponding to the 2, 4, 5, 6 or 7 position in the IAA chemical structure.

The term auxinic analogue(s) of IAA or IAA analogue or IAA auxinic analogue as used herein refers to a mono- or multi-substituted IAA that comprises, for example, one or more of the groups including a halo-, an alkyl-, an alkoxy-, an acyl-, an acylamido-, an acyloxy- and the like.

As used herein, the analogues include not only the free acid form but also an amide, an ester or a salt form of the mono- or multi-substituted IAA analogues.

A halo-group refers to a halogen including, but not limited to, iodo-, bromo-, chloro- and fluoro-groups.

An alkyl-group includes, but is not limited to, an alkyl, R—, (linear, branched or cyclic; saturated or unsaturated), wherein R has 1–10 carbon atoms.

An alkoxy-group includes, but is not limited to, an alkoxy, R—O—(linear, branched or cyclic; saturated or unsaturated), wherein R has 1–10 carbon atoms.

An acyl-group includes, but is not limited to, an acyl, R—C(O)—(linear, branched or cyclic; saturated or unsaturated), wherein R has 1–10 carbon atoms.

An acylamido-group includes, but is not limited to, an acylamido, R—C(O)—NH—(linear, branched or cyclic; saturated or unsaturated), wherein R has 1–10 carbon atoms.

An acyloxy-group includes, but is not limited to, an acyloxy, R—C(O)—O—(linear, branched or cyclic; saturated or unsaturated), wherein R has 1–10 carbon atoms.

The term plant growth regulator or hormone as used herein refers to a naturally occurring or synthetic compound that acts as a hormone in regulating plant growth. Plant growth regulators are exemplified by auxins, cytokinins and gibberellins.

The term auxin or cytokinin as used herein refers to a plant growth regulator that affects the growth of plants. An auxin is exemplified by a compound such as indole-3-acetic acid (IAA), indole-3-butyric acid (IBA), 2,4-dichlorophenoxyacetic acid (2,4-D), naphthaleneacetic acid (NAA), 5,6-dichloroindole-3-acetic acid (5,6-$Cl_2$-IAA) and the like. A cytokinin is exemplified by a compound such as 6-benzylamino purine (BAP), $N^6$.($\Delta_2$ isopentenyl) adenine (2iP), isopentenylpyrophosphate (ipp), 6-(4-hydroxy-3-methyl-2-transbetenylamino)purine (zeatin), 6-furfurylaminopurine (kinetin) and the like. A compound can be tested for auxin activity using a bioassay, e.g., the elongation of coleoptiles of *Avena sativa* (Bottger et al. (1978) Planta 140:89) or the root growth inhibition of Chinese cabbage (Marumo et al. (1974) in *Plant Growth Substance*, p. 419, Hirokawa Publishing Co., Inc., Tokyo) or the hypocotyl swelling of mung bean (Marumo et al. (1974) supra). Cytokinin activity may be measured in assays designed to evaluate the promotion of growth in plants (e.g., tobacco bioassays, etc.) as is well known in the art (Skoog et al. 1967) Phytochem 6:1169–1192; Morris (1986) Ann. Rev. Plant Physiol. 37:509–538; Horgan (1984) in Advanced Plant Physiol (Wilkins, M. B., ed.) pp. 53–75, Pitman Publishing, London; Letham and Palni (1983) Ann. Rev. Plant Physiol 34:163–197; and Chen (1981) in *Metabolism and Molecular Activities of Cytokinins* (Guern, J. and Peaud-Lenoel, C., eds., Springer, N.Y., pp. 34–43). Variations of the cytokinin/auxin concentration ratio cause the enhancement in plant growth to occur preferentially in certain tissues. For example, a high cytokinin/auxin ratio promotes growth of shoots, whereas a low cytokinin to auxin ratio promotes the growth of roots (Depicker et al. (1983) in Genetic Engineering of Plants, T. Kosunge, C. P. Meredith and A. Hollaender, eds., Plenum Press, New York, p. 154).

The term medium or media as used herein refers to a solid or liquid comprising nutrient sufficient to support plant cell growth, the regeneration of plant cells and tissues, and the transformation of plant cells and tissues.

The term carrier as used herein refers to a chemically- or biologically- or physiologically-acceptable molecule that is hydrophobic of hydrophilic or amphoteric and that is useful in facilitating the effectiveness of an active ingredient (i.e., an IAA analogue of the invention) in a plant.

The term a plant as used herein refers to a whole plant or a part of a plant comprising, for example, a locus of a plant, a cell of a plant, a tissue of a plant, an explant, or seeds of a plant. This term further contemplates a plant in the form of a suspension culture or a tissue culture including, but not limited to, a culture of calli, protoplasts, embryos, organs, organelles, etc.

The term transformed plant or transformed plant tissues as used herein refers to introduction of a nucleic acid molecule, e.g., native of foreign DNA, into a plant or plant tissue by transformation or protoplast fusion.

The term transgenic plant or transgenic plant tissue as used herein refers to a plant or plant tissue stably transformed with a foreign gene.

The term transient expression refers to a plant or plant tissue transformed with a DNA, where that DNA is expressed only for a short period of time immediately after transformation.

The term genetic engineering as used herein refers to the introduction of foreign, often chimeric, genes into one or more plant cells which can be regenerated into whole, sexually competent, viable plants which can be self-pollinated or cross-pollinated with other plants of the same species so that the foreign gene, carried in the germ line, can be inserted into or bred into agriculturally useful plant varieties.

The term regeneration as used herein refers to the production of at least one newly developed or regenerated plant tissue, e.g., root, shoot, callus, etc., from a cultured plant tissue or unit, e.g., leaf disc, seed, etc.

The terms percent regeneration, % regeneration or regeneration efficiency as used herein refer to the number of tissue cultured plant units producing at least one newly developed or regenerated tissue as a percentage of the total number of tissue cultured plant units, e.g., $$\left(\frac{\text{number of leaf discs with shoots}}{\text{total number of leaf discs}} \times 100\right).$$

The terms affecting plant growth or growth affecting or affector or affect as used herein refer to any one of a number of plant responses which improve or change, relative to what is observed in the absence of the growth regulator, some characteristic of overall plant growth, for example, stimulation of seed germination, inducing rooting, suppressing shooting, promoting cell proliferation, stimulating callus growth, etc.

The term effective amount as used herein refers to the amount or concentration of a compound that is a plant growth regulator or hormone administered to a plant such that the compound stimulates or invokes one or more of a variety of plant growth responses. A plant growth response includes, among others, the induction of stem elongation, the promotion of root formation, the stimulation of callus formation, enhancement of leaf growth, stimulation of seed germination, increase in the dry weight content of a number of plants and plant parts, and the like.

The present invention relates to the discovery that mono and multi-substituted IAA analogues have utility as auxins in affecting plant growth. For example, in combining 5-bromo-IAA with cytokinin, both callus and shoot formation are observed [disclosed in copending U.S. application Ser. No. 08/430,209 filed Apr. 27, 1995].

IAA auxinic analogues are compared to IAA in functioning as an auxin in both monocots and dicots. For example, it was found that 5-bromo-IAA was between two and four times more effective than IAA in stimulating the regeneration of green calli from *Arabidopsis thaliana*.

Growth affecting compositions of the present invention comprise an IAA analogue, or a mixture of an IAA analogue and one or more additional plant growth regulators, such as cytokinin, gibberellin or the like, mixed with a carrier or auxiliary nutrients. The use of BAP, 2iP and kinetin with an IAA analogue is also exemplified in particular embodiments of this invention. It is contemplated that other cytokinins or other plant growth regulators known to the art can be utilized with an IAA analogue to make a growth affecting composition of the invention. It is also contemplated that more than one cytokinin or a different plant growth regulator (e.g., gibberellin, etc.) can be admixed with an IAA analogue to make a growth enhancing composition of the invention. Also, the choice of plant growth regulator can be varied at different stages of the incubation or application cycles characterizing the growth of a particular plant. Plant growth regulators are known to the art and include, but are not limited to, BAP, 2iP, ipp, zeatin, kinetin, gibberellin, and the like, as described in Skoog et al. (1967) Phytochemistry 6:1169–1192 and Theologis (1989) in *Plant Biotechnology* (Kung and Arntzen, eds.) Butterworth Publishers, Stoneham, Mass.

The mechanism by which the compounds and compositions of the present invention affect the growth cycle of plants and plant tissues is not fully understood at present but it is apparent, as will be demonstrated hereinafter, that they play a significant role in inducing a number of growth affecting responses in a variety of plant species.

In particular embodiments of the invention, various IAA analogues were screened for auxinic activity by incubating different plant tissues, e.g., tobacco and tomato leaf discs and potato stems in (a) MS complete medium (obtained from Life Technologies, Inc., Gaithersburg, Md.) containing different concentrations of auxin only and (2) the MS complete auxin medium containing different ratios of cytokinin/auxin.

Figure 9:
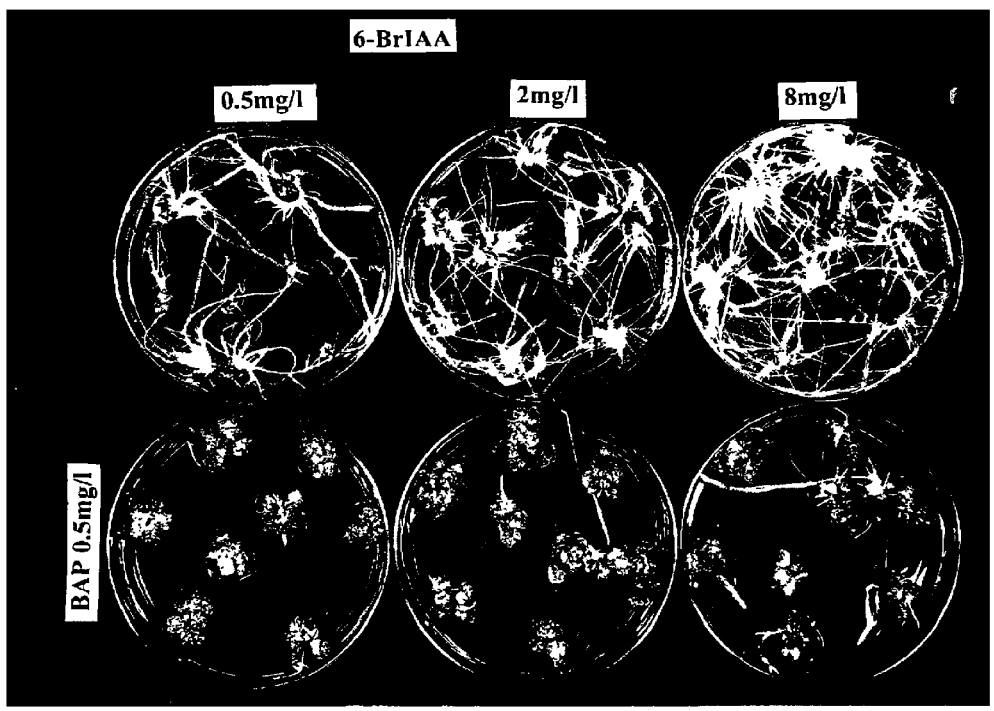
FIG. 9 documents potato plant growth with increasing concentrations of 6-BrIAA (0.5, 2.0 and 8.0 mg/l) in the absence (top row) and in the presence (bottom row) of BAP (0.5 mg/l) on the formation of roots (top row) and calli (bottom row).

In a specific embodiment, tomato leaf discs, tobacco leaf discs and potato stems were incubated in the MS complete medium comprising different amounts (i.e., 0.5, 2.0 and 8.0 mg/l) of 6-BrIAA in the absence and presence of a cytokinin, e.g., BAP (0.5 mg/l). For tomato leaf discs, when only 6-BrIAA was present in the incubation mixture, only root formation was observed from the tomato leaf discs. FIG. 9, upper row, shows the direct correlation between root formation from tomato leaf discs and increasing concentration of 6-BrIAA. However, as shown in FIG. 9, lower row, when the tomato leaf discs were incubated in the MS complete medium containing 0.5 mg/l BAP and 0.5, 2.0 or 8.0 mg/ml of 6-BrIAA, calli, not roots, were formed in each case.

Figure 8:
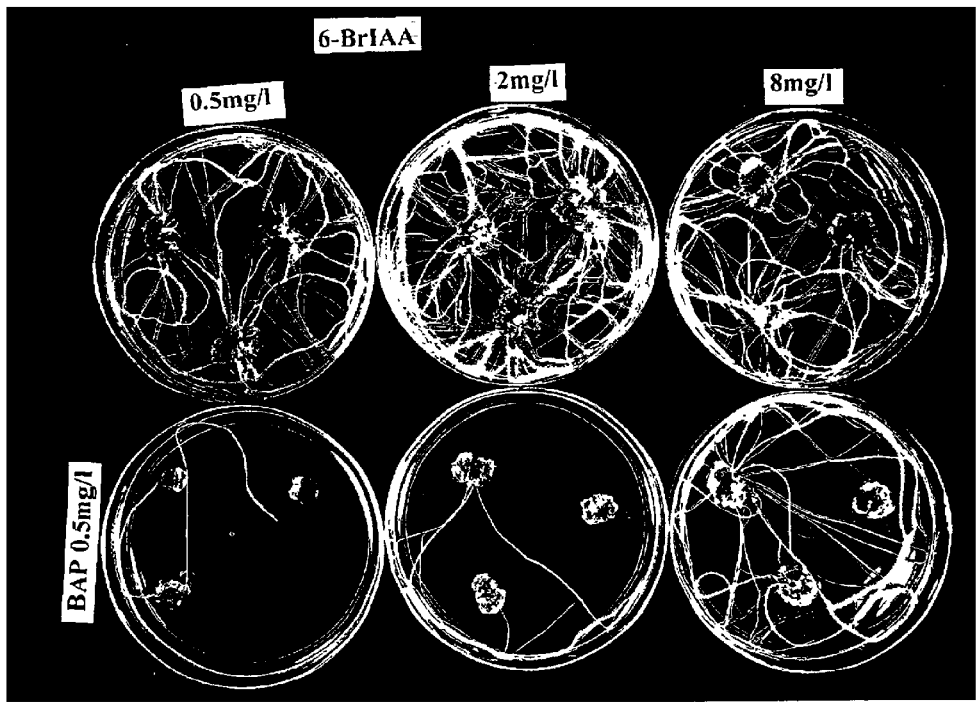
FIG. 8 documents tomato plant growth with increasing concentrations of 6-BrIAA (0.5, 2.0 and 8.0 mg/l) in the absence (top row) and in the presence (bottom row) of BAP (0.5 mg/l) on the formation of roots (top row) and calli (bottom row).

When the same auxin and cytokinin conditions were applied to potato stems (FIG. 8) and tobacco leaf discs (FIG. 10), different growth responses were observed. In potato, root formation increased as the concentration of 6-BrIAA increased from 0.5 to 2.0 mg/l, but at a concentration of 8.0 mg/ml, root formation was diminished (FIG. 8, upper row). When BAP (0.5 mg/l) was present in the incubation mixture, callus formation was observed at all ratios of cytokinin/auxin (FIG. 9, lower row). In contrast, when tobacco leaf discs were exposed to different concentrations of 6-BrIAA in the absence of BAP (FIG. 10, upper row), both the formation of roots and the formation of calli were observed, while in the presence of both 6-BrIAA and BAP (FIG. 10, lower row), the formation of both shoots and calli occurred. These results indicate that different plant tissues have different responses to the auxin treatment, and that the concentration of auxin influenced the regeneration of plant tissues both qualitatively and quantitatively.

In another embodiment of the invention, IAA analogues were screened for auxinic activity. IAA derivative structures such as 2-bromoindole-3-acetic acid (2-BrIAA), 6-bromoindole-3-acetic acid (6-BrIAA), 7-bromoindole-3-acetic acid (7-BrIAA), 5-chloroindole-3-acetic acid (5-ClIAA), 5-fluoroindole-3-acetic acid (5-FIAA), 7-fluoroindole-3-acetic acid (7-FIAA), 5-iodoindole-3-acetic acid (5-IIAA), 5-ethylindole-3-acetic acid (5-EtIAA), 7-ethylindole-3-acetic acid (7-EtIAA), and 5-methoxyindole-3-acetic acid (5-MeOIAA) were tested for the ability to function as an auxin in the regeneration of plant tissues in comparison to auxin standards in the art such as IAA and NAA. Table 1 documents the ability of the different IAA analogues to stimulate the regeneration of roots or calli from tobacco, tomato and potato. In general, IAA analogues having a bromine substitution at the 2

TABLE 1

Regeneration of roots or calli from different plant tissues using IAA analogues

| Auxins 2 mg/l | Tobacco | | Tomato | | Potato | |
|---|---|---|---|---|---|---|
| | Roots | Callus | Roots | Callus | Roots | Callus |
| NAA | + | + | +++ | − | + | +++ |
| IAA | ++++ | + | +++ | − | +++ | ++ |
| 2-BrIAA | ++++ | ++ | + | − | +++ | +++ |
| 6-BrIAA | +++ | +++ | ++++ | + | ++++ | ++ |
| 7-BrIAA | ++++ | ++ | ++++ | − | +++ | + |
| 5-ClIAA | +++ | ++ | + | + | − | ++++ |
| 5-FIAA | ++++ | + | +++ | − | ++++ | + |
| 7-FIAA | ++++ | +++ | ++ | + | NA | NA |
| 5-IIAA | + | +(−) | ++ | − | +(−) | − |
| 5-EtIAA | + | +(−) | ++ | − | ++ | − |
| 7-EtIAA | − | + | − | − | ++++ | − |
| 5-MeoIAA | ++ | ++ | − | + | ++ | ++ |

NA = not available.
+(−) means preliminary observation.

or 6 or 7 position or a fluorine substitution at the 5 or 7 position appear to exhibit auxinic activity that was equal to or better than that observed for IAA.

These IAA derivatives were further evaluated for auxinic activity in the presence of a cytokinin. Table 2 indicates the ability of the different IAA analogues (at a concentration of 2 mg/l) in the presence of BAP (at a concentration of 0.5 mg/l) to stimulate the regeneration of shoots and/or calli from tobacco, tomato and potato. Incubation of plant tissues

TABLE 2

Regeneration of shoots or calli from different plant tissues using IAA analogues together with cytokinin

| BAP 0.5 mg/l + Auxins | Tobacco | | Tomato | | Potato | |
|---|---|---|---|---|---|---|
| 2 mg/l | Callus | Shoots | Callus | Shoots | Callus | Shoots |
| NAA | ++++ | − | ++++ | − | +++ | − |
| IAA | + | ++++ | +++ | + | ++ | − |
| 2-BrIAA | ++ | ++ | + | − | ++ | − |
| 6-BrIAA | +++ | + | ++++ | − | +++ | − |
| 7-BrIAA | + | ++++ | ++++ | − | + | − |
| 5-ClIAA | +++ | − | +++ | + | ++ | − |
| 5-FIAA | +++ | ++ | ++++ | + | + | − |
| 7-FIAA | ++++ | ++ | ++++ | − | NA | NA |
| 5-IIAA | +(−) | +++ | + | − | +(−) | − |
| 5-EtIAA | − | +++ | +++ | − | + | − |
| 7-EtIAA | − | ++++ | +++ | − | + | − |
| 5-MeoIAA | − | ++++ | ++ | − | ++ | − |

NA = not available.
+(−) means preliminary observation in the presence of both auxin and cytokinin promoted callus formation in all three plants tested, i.e., tobacco, tomato and potato, whereas shoots were produced only in tobacco and not in tomato and potato incubated with both auxin and cytokinin. In general, the halogenated IAA analogues were comparable to IAA in inducing the regeneration of calli in tobacco, while alkyl-IAA and alkoxy-IAA analogues showed auxinic activity similar to that of IAA in tomato and potato under these conditions.

These IAA analogues were further evaluated for their abilities to effect the regeneration of plant tissues comprising foreign DNA. Tobacco and potato tissues were subjected to *Agrobacterium*-mediated transformation techniques, including cocultivation with *Agrobacterium* containing pBI121 and selecting with MS complete medium containing 0.5 mg/l BAP, 2 mg/l IAA derivative and 100 mg/l kanomycin. Table 3 indicates that the IAA analogues tested (7-BrIAA, 5-ClIAA, 5-FIAA, 7-FIAA, 5-EtIAA, 7-EtIAA and 5-MeOIAA), in the presence of BAP, stimulated the regeneration of kanamycin resistant calli in transformed tobacco and potato, and shoots in transformed tobacco. In general, halogenated-IAA, alkyl-IAA and alkoxy-IAA derivatives exhibited IAA-type auxinic activities in transgenic plant tissues.

Further, examples of IAA analogues of the invention were evaluated for auxinic activity in the presence of a cytokinin. Table 4 indicates the ability of 2-BrIAA, 6-BrIAA, 7-BrIAA, 5-FIAA, 5-EtIAA and 7-EtIAA (at a concentration of 2 mg/l) in the presence of 0.5 mg/l of BAP to stimulate the regeneration of shoots and callus from cassava leaves and stems. It was also shown that 5-FIAA promoted the formation of shoots in cassava stems and to a greater extent from cassava leaves.

Figure 11:
FIG. 11 documents cassava plant growth in the presence of 5-FIAA or 7-FIAA (2.0 mg/l) and BAP (0.5 mg/l) on shoot formation.

In another embodiment of the invention, IAA analogues of the present invention were applied to the regeneration of plant tissues known in the art to be difficult to regenerate, such as cassava, woody plants, and monocotyledonous crops [Vasil and Vasil (1994) in *Plant Cell and Tissue Culture* (Vasil and Thorpe, eds.), Kluwer Academic Publishers, Dordrech, Netherlands; Chee (1995) Plant Cell Reports 14:753–757; Bums and Schwartz (1996) Plant Cell Reports 15:405–408; Mihaljevic et al. (1996) Plant Cell Reports 15:610–614; Schopke et al. (1996) Nature Biotechnology 14:731]. FIG. 11 documents the regeneration of shoots in cassava leaves and stems incubated in MS complete medium comprising 2 mg/l of 5-FIAA and 0.5 mg/l BAP.

TABLE 3

Regeneration of Agrobacterium-mediated transformed plant tissues using IAA analogues

| BAP 0.5 mg/+ | Tobacco | | Potato | |
|---|---|---|---|---|
| | Callus | Shoots | Callus | Shoots |
| NAA | ++ | + | ++ | − |
| IAA | ++ | + | + | − |
| 7-BrIAA | ++ | + | +(−) | − |
| 5-ClIAA | +++ | ++ | ++ | − |
| 5-FIAA | +++ | ++ | + | − |
| 7-FIAA | +++ | + | +(−) | − |
| 5-EtIAA | + | ++ | + | − |
| 7-EtIAA | + | ++ | +(−) | − |
| 5-MeoIAA | ++ | ++ | + | − |

+(−) means preliminary observation.

TABLE 4

Regeneration of shoots or calli from Cassava
Leaves and Stems with IAA Analogues in the Presence of Cytokinin

| BAP 0.5 mg/+ | Stems | | Leaves | |
|---|---|---|---|---|
| Auxin 2 mg/l | Callus | Shoots | Callus | Shoots |
| NAA | +++ | − | +++ | − |
| 2-BrIAA | ++ | − | + | − |
| 6-BrIAA | +++ | − | NT | NT |
| 7-BrIAA | ++ | − | +++ | − |
| 5-FIAA | +++ | + | ++ | +++ |
| 5-EtIAA | ++ | − | + | − |
| 7-EtIAA | + | − | NT | NT |

Traditionally, in order to achieve shoot regeneration from cassava leaves and stems, the cassava tissue is transferred from a medium containing a high amount of auxin to another medium containing auxin and cytokinin. In the present invention, the regeneration of shoots from cassava tissue was obtained without tissue transfer from a high auxin medium to a medium containing auxin and cytokinin. In addition, the regeneration of shoots in cassava tissue, according to the invention, showed significant improvement in the number of shoots regenerated. Thus, the IAA analogues of the present invention not only exhibit auxinic activity but also improve the yield of plant tissue regenerated, as exemplified in plant tissues traditionally described as being difficult to regenerate, e.g., cassava, woody plants, maize, soybean, wheat, etc.

The practice of the present invention contemplates a wide variety of plant growth responses, including stimulation of seed germination and breaking of dormancy; increasing yields; hastening ripening and color production in fruit; increasing flowering and fruiting; stimulating shoot formation; inducing callus development; inducing rooting and causing cell proliferation; increasing the hardiness of various plant species; and increasing the dry weight content of a number of plants and plant parts. In addition to these categories of responses, any other modification of a plant, seed, fruit or vegetable, so long as the net result is to increase the growth or maximize any beneficial or desired property of the agricultural and horticultural crop or seed, is intended to be included within the scope of advantageous responses achieved by the practice of the present invention.

Suitable applications of the growth enhancing compositions of the present invention to cultures of plant tissues induce the regeneration of shoots, roots or calli. This effect occurs in both monocotyledonous and dicotyledonous plant species and applies to a wide variety of plants.

The compositions of the instant invention are further utilized for plant regeneration from transgenic plants.

Genetic engineering of plants generally involves two complementary processes. The first process involves the genetic transformation of one or more plant cells of a specifically characterized type. By transformation it is meant that a foreign gene, typically a chimeric gene construct, is introduced into the genome of the individual plant cells, typically through the aid of a vector which has the ability to transfer the gene of interest into the genome of the plant cells in culture. The second process then involves the regeneration of the transformed plant cells into whole sexually competent plants. Neither the transformation nor regeneration process need be 100% successful but must have a reasonable degree of reliability and reproducibility so that a reasonable percentage of the cells can be transformed and regenerated into whole plants.

The two processes, transformation and regeneration, must be complementary. The complementarity of the two processes must be such that the tissues which are successfully genetically transformed by the transformation process must be of a type and character, and must be in sufficient health, competency and vitality, so that they can be successfully regenerated into whole plants.

Successful transformation and regeneration techniques have been demonstrated for monocots and dicots in the prior art. For example, the transformation and regeneration of tobacco plants was reported in Barton et al., Cell 32:1033 (April 1983), whereas the regeneration of cotton is described in Umbeck, U.S. Pat. No. 5,004,863, issued Apr. 2, 1991. Further, transformation and regeneration of rice was described by Abdullah et al. (1986) Bio/Technology 4:1087–1090, whereas maize was transformed and regenerated as described in Rhodes et al. (1988) Bio/Technology 6:56–60 and Science 240:204–207.

The most common methodology used for the transformation of cells of dicot plant species involves the use of the plant pathogen *Agrobacterium tumefaciens*. Although *Agrobacterium*-mediated transformation has been achieved in some monocots, other methods of gene transfer have been more effective, e.g., the polyethylene glycol method, electroporation, direct injection, particle bombardment, etc., as described by Wu in *Plant Biotechnology* (1989) pp. 35–51, Butterworth Publishers, Stoneham, Mass. The present invention will be useful with any method of transformation that includes plant regeneration steps.

In a specific embodiment, the invention envisions the genetic transformation of tissues in culture derived from leaf discs or hypocotyl explants. The transformed tissues can be induced to form plant tissue structures, which can be regenerated into whole plants.

The transformation technique of the present invention is one which makes use of the Ti plasmid of *A. tumefaciens*. In using an *A. tumefaciens* culture as a transformation vehicle, it is most advantageous to use a non-oncogenic strain of the Agrobacterium as the vector carrier so that normal non-oncogenic differentiation of the transformed tissue is possible. To be effective once introduced into plant cells, the chimeric construction including a foreign gene of interest must contain a promoter which is effective in plant cells to cause transcription of the gene of interest and a polyadenylation sequence or transcription control sequence also recognized in plant cells. Promoters known to be effective in plant cells include the nopaline synthase promoter, isolated from the T-DNA of *Agrobacterium*, and the cauliflower mosaic virus 35S promoter. Other suitable promoters are known in the art. It is also preferred that the vector which harbors the foreign gene of interest also contain therein one or more selectable marker genes so that the transformed cells can be selected from non-transformed cells in culture. In many applications, preferred marker genes include antibiotic resistance genes so that the appropriate antibiotic can be used to segregate and select for transformed cells from among cells which are not transformed.

The details of the construction of the vectors containing such foreign genes of interest are known to those skilled in the art of plant genetic engineering and do not differ in kind from those practices which have previously been demonstrated to be effective in tobacco, petunia and other model plant species. The foreign gene should obviously be selected as a marker gene (Jefferson et al. (1987) EMBO J. 6:3901–3907) or to accomplish some desirable effect in plant cells. This effect may be growth promotion, disease resistance, a change in plant morphology or plant product quality, or any other change which can be accomplished by genetic manipulation. The chimeric gene construction can code for the expression of one or more exogenous proteins, or can cause the transcription of negative strand RNAs to control or inhibit either a disease process or an undesirable endogenous plant function.

To initiate the transformation and regeneration process for plant tissues, it is necessary to first surface sterilize tissues to prevent inadvertent contamination of the resulting culture. If the tissues are seeds, the seeds are then allowed to germinate on an appropriate germinating medium containing a fungicide. Four to ten days after germination the hypocotyl portion of the immature plant is removed and sectioned into small segments averaging approximately 0.5 centimeters apiece. The hypocotyl explants are allowed to stabilize and remain viable in a liquid or agar plant tissue culture medium.

Once the tissues have stabilized, they can promptly be inoculated with a suspension culture of transformation competent non-oncogenic *Agrobacterium*. The inoculation process is allowed to proceed for a short period, e.g., two days, at room temperature, i.e., 24° C.

At the end of the inoculation time period, the remaining treated tissues can be transferred to a selective agar medium, which contains one or more antibiotics toxic to *Agrobacterium* but not to plant tissues, at a concentration sufficient to kill any *Agrobacterium* remaining in the culture. Suitable antibiotics for use in such a medium include carbenicillin, cefotaxime, etc. as the bactericide for *Agrobacterium* and kanamycin as the selective antibiotic for transformed plant tissues.

The tissues are now cultivated on a tissue culture medium which, in addition to its normal components, contains a selection agent. The selection agent, exemplified herein by kanamycin, is toxic to non-transformed cells but not to transformed cells which have incorporated genetic resistance to the selection agent and are expressing that resistance. A suitable tissue culture medium is the MS medium to which are added an auxinic analogue of the invention and a cytokinin, with or without antibiotics. The surviving transformed tissues are transferred to a secondary medium to induce tissue regeneration. The surviving transformed tissue will thus continue to be regenerated into a whole plant through the regeneration technique of the present invention or through any other alternative plant regeneration protocols.

The precise amount of growth affecting compositions employed in the practice of the present invention will depend upon the type of response desired, the formulation used and the type of plant treated. The invention contemplates the use of a ratio of cytokinin concentration to auxin concentration of between approximately 50.0 and 0.001, and preferably between approximately 5.0 and 0.05, and more preferably between approximately 2.0 and 0.25.

The chemical compounds employed as active components of the growth enhancing compositions of the present invention may be prepared in accordance with processes well known in the prior art or may be obtained commercially from readily available sources.

The IAA analogues of the invention are useful in making a plant less susceptible to the toxicities of antibiotics. Such IAA analogues are also useful in enabling plants to overcome stress, e.g., environmental stress, physical stress, chemical stress, pollution, contamination, drought, light, and the like.

The present compositions may be applied at any developmental stage of the plant species to obtain plant hormone or maintenance effects throughout maturity and to expedite regrowth in damaged tissues during early developmental stages, depending upon the concentration used, the formulation employed and the type of plant species treated.

The compositions of the present invention are preferably used in conjunction with specific auxiliary nutrients or other plant growth regulators in precise proportions to achieve a particular synergistic, growth enhancing response in various type of plants. The present compositions may additionally be used in association with fungicides to increase the disease resistance of various plants, making the plant tissue resistant to invasion by pathogens by influencing the enzyme and plant processes which regulate natural disease immunity. While the present compositions possess essentially no phytotoxic activity of their own, they may sometimes be used in conjunction with herbicides to stimulate the growth of unwanted plants in order to make such plants more susceptible to a herbicide. However, it is preferred to regard the results achieved in the practice of the present invention as growth enhancing responses in agricultural and horticultural crops, as well as perennial and annual household plants species.

The following examples are illustrative of the wide range of plant growth responses that can be realized by application of a preferred composition of the present invention to various plant species. Nevertheless, there is no intention that the invention be limited to these optimum ratios of active components since workers in the art will find the compositions of the invention set forth hereinabove to be effective growth enhancers. Also, it should readily occur to one skilled in the art that the recognition of improved results using the compositions according to the present invention in connection with other plants, seeds, fruits and vegetables not specifically illustrated herein is readily within the capabilities of one skilled in the art. The following examples serve to illustrate the utility of the invention without limiting its scope.

EXAMPLES

Example 1

Chemical Synthesis of an IAA Auxinic Analogue (A) Synthesis of an Halogenated IAA The synthesis of monohalogenated IAA compounds is based primarily on the Fischer indole synthesis method as put forth by J. March in *Advanced Organic Chemistry* (1985) J. Wiley and Son, p. 1032–1033. This method depends upon Fischer ring closure of the proper 3-formylpropionic acid phenyl hydrazone. The general availability of substituted phenylhydrazine has made this method attractive for the preparation of the indole-3-acetic acids substituted in the benzene ring (Fox and Bullock (1951) J. Am. Chem. Soc. 73:2756 and Hatano et al. (1987) Experientia 43:1237).

Alternatively, a large variety of substituted anilines are available and can be used as starting materials to synthesize corresponding substituted phenylhydrazines which, in turn, can be converted to substituted IAA compounds. Substituted anilines can be converted to corresponding substituted phenylhydrazines by the method of Robinson (1957) Can. J. Chem. 35:1570.

Use of the 2- and 4-halogen substituted phenylhydrazine with the 3-formylpropionic acid gives rise to a 2- and 4-halogen substituted phenylhydrazone which cyclizes to the corresponding 7- and 5-halo-IAA, respectively. Preparation of the 3-halogen substituted phenylhydrazone cyclizes to form the 4- and 6-halo-IAA isomers which can be separated using $C_{18}$ reverse phase HPLC by elution with water:methanol:acetic acid. The 4-halo-IAA is eluted out in advance of the 6-halo-IAA. A 2-halo-IAA compound can be synthesized by the procedure described by Porter and Thimann (1965) 4:229–243. Each isomeric product can be identified using thin layer chromatography, mass spectroscopy and nuclear magnetic resonance.

Both a 4-halo-IAA and a 6-halo-IAA compound can be synthesized individually by the method of Majima and Hoshino (1925) Ber 58:2042 as described by Fox and Bullock (1951) J. Am. chem. Soc. 73:2756. The 4- and 6-chloroindolylmagnesium iodide complexes are condensed with chloroacetonitrile and the resulting nitrites are hydrolyzed to the corresponding indole-3-acetic acids.

The protocol for the synthesis of a monosubstituted halogen-IAA comprises the following steps. A substituted phenylhydrazine HCl (0.05 mole) is dissolved in 30% acetic acid, pH 4.0, and is added to 0.1 mole 3-formylpropionic acid solution that is freshly-prepared (See below). After cooling, the precipitate is collected and dissolved in 75 ml pyridine. To the solution, 100 ml of concentrated HCl and 25 ml of 85% $H_3PO_4$ are added and the resultant solution is refluxed for 10 hours in the dark under $N_2$.

The reaction mixture is diluted with 600 ml $H_2O$, filtered and the filtrate is extracted with ether several times. The ether fractions are pooled and washed with water. The indole acetic acid is extracted back into 0.5 M NaOH (200 ml), boiled and precipitated with concentrated HCl (pH 1.0). Soapy tars are decanted or filtered off. The substituted IAA is recrystallized twice from $H_2O$, $H_2O$/ethanol, toluene or ethyl acetate/hexane.

3-formylpropionic acid is freshly prepared by adding 200 ml of fresh 1 M NaOCl solution to 24.9 g (0.20 mole) of glutamic acid in 400 ml of 0.5 N NaOH solution, stirring until it gives a negative test with starch-iodide paper and is then acidified by adding 70 ml of 3N HCl.

Multi-halogenated IAA compounds can be synthesized according to the guidelines provided by the methods of Engvild (1977) Acta Chem. Scand. B31:338 (e.g., 4,6-, 4,7-, 5,7-, 6,7-dichloro-IAAs), or the method of Baldi et al. (1985) J. Label. Compd. Radiopharm. 22:279 (e.g., 5,6-, 4,5-dichloro-IAAs) or the method of Hatano et al. (1987) Experientia 43:1237–1239 (e.g., 5,6-, 6,7-, 4,5-, 4,6-, 5,7-, 4,7-dichloro-IAA), etc.

(B) Synthesis of an Alkyl-, Alkoxy-, Acyl-, Acylamido- and Acyloxy-IAA

The procedure outlined above (Example 1(A)) is used to prepare monosubstituted IAA compounds having an alkyl-, alkoxy-, acyl-, acylamido- or acyloxy-substituted group at the 2, 4, 5, 6 or 7 position. The synthetic reaction is carried out using the appropriate substituted phenylhydrazine in order to obtain the desired substituted IAA compound. Where necessary, a reactive substituent group, e.g., acyl-, acylamido-, acyloxy-, etc., may be protected during the synthetic process after which it is deprotected.

Multi-substituted IAA analogues have 2 or more different substituents selected from halo-, alkyl-, alkoxy-, acyl-, acylamido-, acyloxy-substituent groups can be synthesized using synthetic techniques well known in the art [Vasil and Vasil (1994) in *Plant Cell and Tissue Culture* (Vasil and Thorpe, eds.), Kluwer Academic Publishers, Dordrech, Netherlands; Chee (1995) Plant Cell Reports 14:753–757; Bums and Schwartz (1996) Plant Cell Reports 15:405–408; Mihaljevic et al. (1996) Plant Cell Reports 15:610–614; Schopke et al. (1996) Nature Biotechnology 14:731). For example, IAA compounds comprising combinations of alkyl-, halo- and acyl-substituent groups (e.g., 2-methyl-5, 7-dichloro-IAA, 2-COOH-5-methyl-IAA, 2-COOH-7-chloro-IAA, etc.) can be prepared according to Fox and Bullock (1951) J. Am. Chem. Soc. 73:2756–2759; Hoffman et al. (1952) J. Biol. Chem. 196:437 and Engvild (1977) Acta Chem. Scand. B31:338–344, etc.

Example 2
Evaluation of Auxin Activity in Non-transgenic Plants
(a) Tobacco

Seeds of *Nicotiana tobaccum* Xanthi are provided by Dr. James Saunders (USDA, Beltsville, Md.). Young tobacco leaves are removed and cut into small pieces. The explants are incubated on (1) MS complete medium (obtained from Life Technologies, Inc., Gaithersburg, Md.) containing different concentrations of auxin related compounds only or (2) MS complete medium containing different concentrations of auxin-related compounds and 0.5 mg/l benzylaminopurine (BAP) using an 18 h light/6 h dark cycle until the formation of green calli and shoots.

(b) Tomato

Tomato seeds of variety "Moneymaker" are provided by Dr. James Saunders (USDA, Beltsville, Md.). Young tomato leaves are removed and cut into small pieces. Explants are incubated in MS complete medium with auxin in the presence or absence of cytokinin as described in section (a) above for tobacco.

(c) Potato

Potato seeds of variety "Kent V. F." are provided by Dr. James Saunders (USDA, Beltsville, Md.). Young potato stems are removed and cut into small pieces. Explants are incubated in MS complete medium with auxin in the presence or absence of cytokinin as described in section (a) above for tobacco.

(d) *Arabidopsis thaliana*

Seeds of *Arabidopsis thaliana* ecotypes Columbia and Landersberg ereta are provided by Dr. Keith Davis (The Ohio State University, Columbus). Tissues of hypocotyl are removed from 10-day-old seedlings, transferred to MS complete medium containing (1) different concentrations of IAA or IAA analogue with different concentrations of $N^6$. ($\Delta_2$Isopentenyl) adenine (2iP) and (2) different concentrations of IAA analogue with different concentrations of 2iP, BAP, or kinetin. The explants are incubated at 23° C. using an 18 h light/6 h dark cycle until the formation of green calli and shoots.

(e) Rice

Seeds of *Oryza sativa* cv. Orion are kindly provided by Dr. James Saunders (USDA, Beltsville, Md.). For rice embryogenic callus formation, the surfaces of the seeds are sterilized as follows: mature seeds are soaked in 0.5% detergent with shaking for 1 h, transferred to a solution containing 20% bleach and 0.1% Tween20® and vacuumed with shaking. The seeds are then rinsed with sterilized distilled water three times. At this point the seeds are transferred onto a MS complete medium containing different concentrations of BAP and different concentrations of IAA analogue, incubated in the dark at 25° C. for 1 month, and then incubated at 25° C. using an 18 h light/6 h dark cycle until the formation of green calli and shoots.

(f) Cassava

Stems or third young leaves were removed from the one month old Cassava plants and cut into small pieces. The explants were incubated on MS complete medium containing different concentrations of auxin related compounds and 0.5 mg/l benzylaminopurine (BAP). The explants were incubated at 23° C. using an 18 hour light/six hour dark cycle until the formation of green calli and shoots.

The regeneration of plant tissues using tissue culture depends on plant hormones such as auxin and cytokinin. It is known that the presence of an auxin in plant tissue cultured on Murashige and Skoog (MS) medium (Murashige, T. and F. Skoog (1962) Physiol. Plant 15:473–497) stimulates the formation of root structure whereas the formation of callus is observed when not only the auxin but also a cytokinin complement the MS nutrient medium. Therefore, evaluation of a test compound as a potential new auxin is performed by incubating tobacco leaf discs in (a) the MS complete medium containing different concentrations of auxin only and (b) the MS complete medium containing different ratios of cytokinin to auxin concentrations (cytokinin/auxin).

Figure 2:
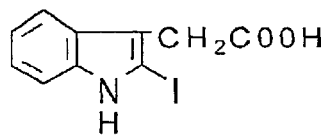
FIG. 2 presents the chemical structures of some halogenated IAA auxinic analogues.
Figure 2:
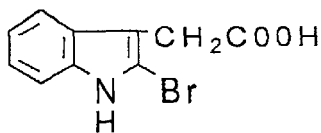
Figure 2:
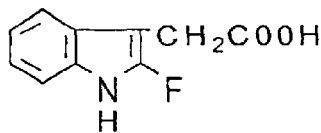
Figure 2:
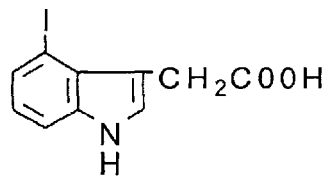
Figure 2:
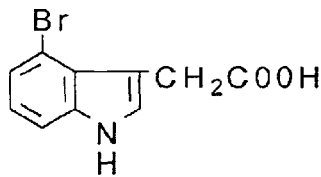
Figure 2:
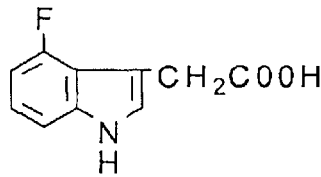
Figure 2:
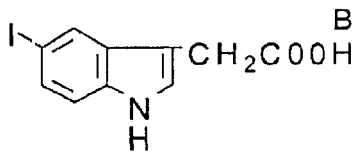
Figure 2:
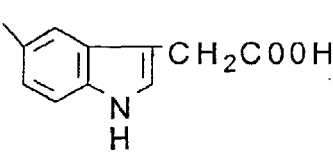
Figure 2:
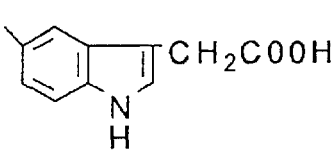
Figure 2:
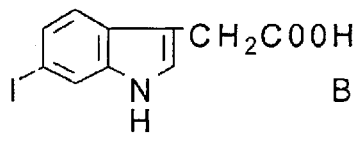
Figure 2:
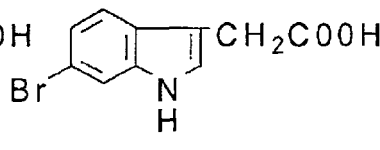
Figure 2:
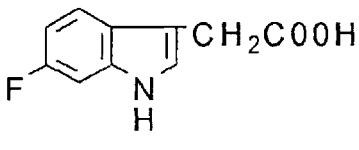
Figure 2:
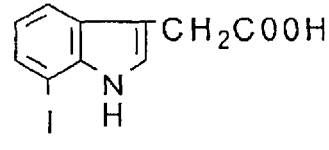
Figure 2:
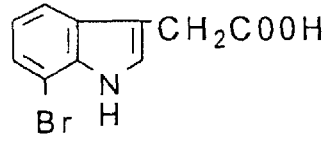
Figure 2:
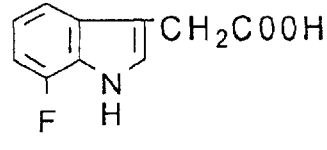

In a particular embodiment of mono-substituted IAA analogues, fifteen halogenated IAA compounds are chemically synthesized and tested for plant growth regulatory activity. As shown in FIG. 2, the following compounds are tested for auxin activity: 2-iodo-IAA, 4-iodo-IAA, 5-iodo-IAA, 6-IAA, 7-iodo-IAA, 2-bromo-IAA, 4-bromo-IAA,5-bromo-IAA,6-bromo-IAA, 7-bromo-IAA, 2-fluoro-IAA, 4-fluoro-IAA, 5-fluoro-IAA, 6-fluoro-IAA and 7-fluoro-IAA. The biological activity of each compound is compared to that of IAA. Different concentrations of each compound are tested for the ability to stimulate root, shoot and callus formation from tobacco and tomato leaf discs and potato stems. The ability to stimulate root formation is evaluated for each compound in the presence of different concentration ratios of cytokinin (e.g., BAP) to test compound.

Figure 3:
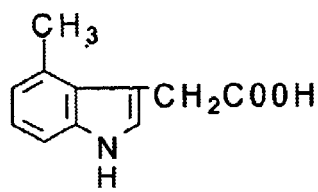
FIG. 3 presents the chemical structures of some monosubstituted, alkyl-IAA auxinic analogues having an alkyl group in the 4 position. The present invention also contemplates alkyl-IAA compounds having the same alkyl substituent group at position 2, 5, 6 or 7. Exemplified in FIG. 3 are alkyl-IAA structures having an alkyl (R) group with 1–4 carbon atoms. The instant invention, however, provides IAA analogues with alkyl substituents with 1–10 carbon atoms.
Figure 3:
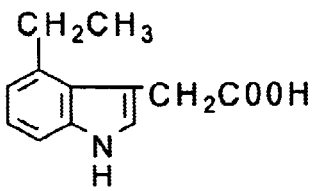
Figure 3:
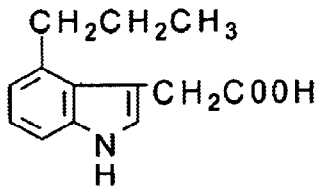
Figure 3:
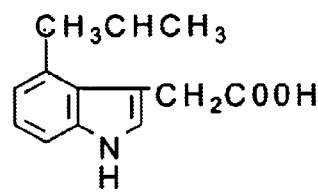
Figure 3:
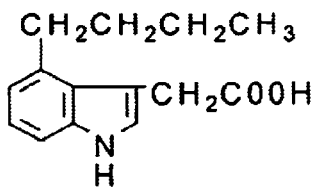
Figure 3:
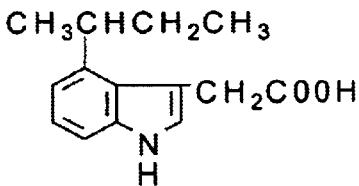
Figure 3:
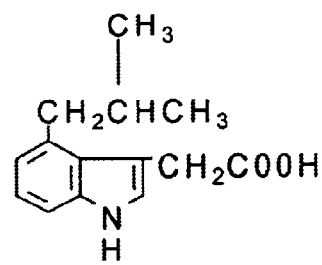
Figure 3:
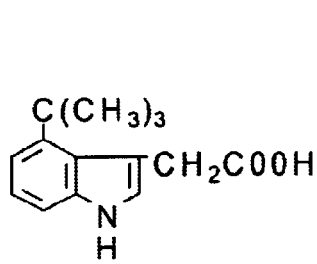
Figure 3:
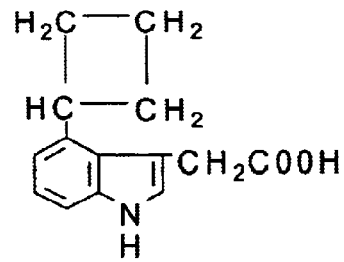

In another embodiment of mono-substituted IAA analogues, alkyl substituted IAA compounds are chemically synthesized and tested for plant growth regulatory activity. Shown in FIG. 3 are nine monosubstituted IAA compounds having an alkyl substituent group at position 4. The present invention also contemplates alkyl-IAA compounds having alkyl substituents with 1–10 carbon atoms and having the same or different alkyl substituent groups at position 2, 5, 6 or 7. The biological activity of each compound is compared to that of IAA. Different concentrations of each compound are tested for the ability to stimulate root, shoot and callus formation from tobacco and tomato and tomato leaf discs and potato stems. The ability to stimulate root, shoot and callus formation is evaluated for each compound in the presence of different concentration ratios of cytokinin (e.g., BAP) to test compound.

Figure 4:
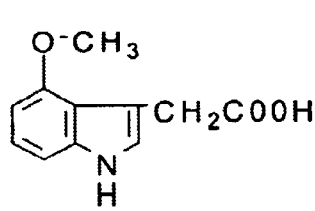
FIG. 4 presents the chemical structures of some monosubstituted, alkoxy-IAA auxinic analogues having an alkoxy group in the 4 position. The present invention also contemplates alkoxy-IAA compounds having the same alkoxy substituent group at position 2, 5, 6 or 7. Exemplified in FIG. 4 are alkoxy-IAA structures having an alkoxy group with 1–4 carbon atoms. The instant invention, however, provides IAA molecules with alkoxy substituents with 1–10 carbon atoms.
Figure 4:
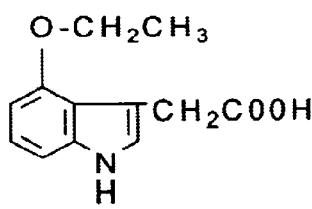
Figure 4:
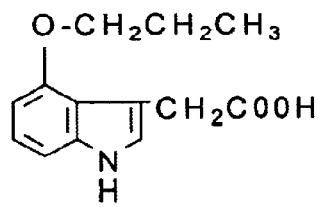
Figure 4:
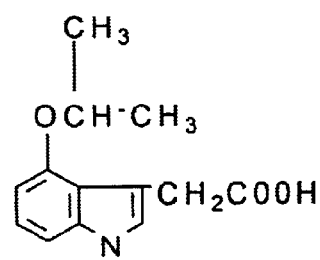
Figure 4:
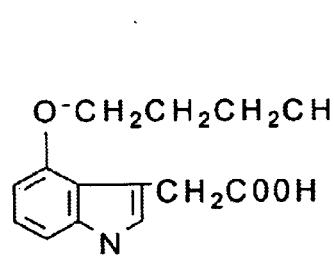
Figure 4:
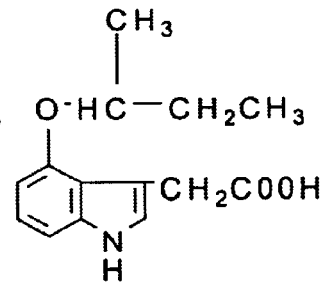
Figure 4:
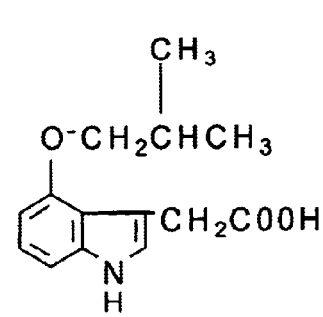
Figure 4:
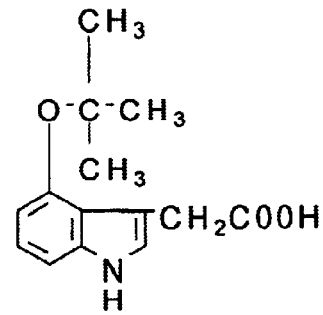
Figure 4:
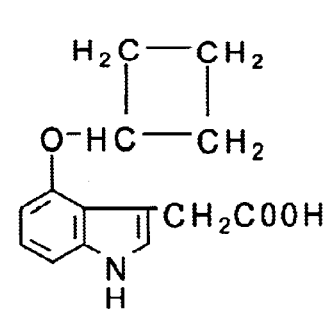

In another embodiment of mono-substituted IAA analogues, alkoxy-substituted IAA compounds are chemically synthesized and tested for plant growth regulatory activity. Shown in FIG. 4 are nine monosubstituted IAA compounds having an alkoxy substituted group at position 4. The present invention also contemplates alkoxy-IAA compounds having alkoxy substituent groups with 1–10 carbon atoms and having the same or different alkoxy substituent groups at position 2, 5, 6 or 7. The biological activity of each compound is compared to that of IAA. Different concentrations of each compound are tested for the ability to stimulate root, shoot and callus formation from tobacco and tomato leaf discs and potato stems. The ability to stimulate root shoot and callus formation is evaluated for each compound in the presence of different concentration ratios of cytokinin (e.g., BAP) to test compound.

Figure 5:
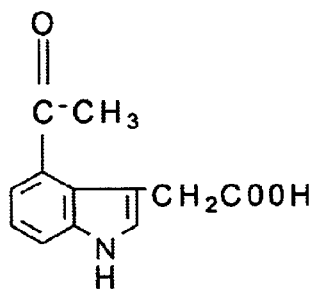
FIG. 5 presents the chemical structures of some monosubstituted, acyl-IAA auxinic analogues having an acyl group in the 4 position. The present invention also contemplates acyl-IAA compounds having the same acyl substituent group at position 2, 5, 6 or 7. Exemplified in FIG. 5 are acyl-IAA structures having an acyl group with 1–4 carbon atoms. The instant invention, however, provides acyl-substituted IAA molecules having acyl groups with 1–10 carbon atoms.
Figure 5:
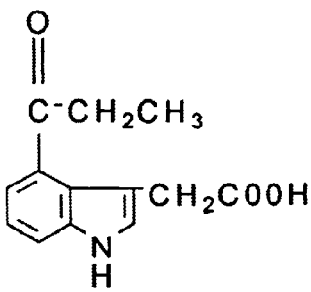
Figure 5:
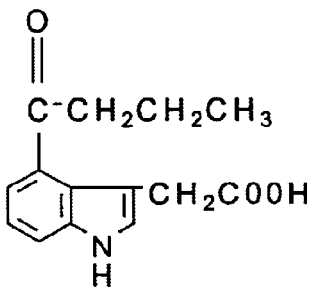
Figure 5:
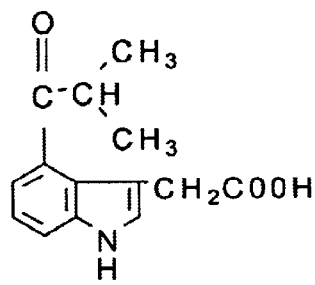
Figure 5:
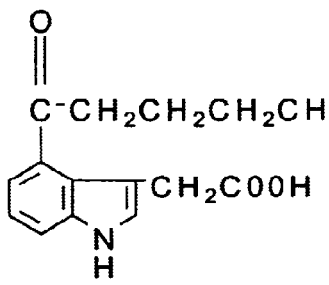
Figure 5:
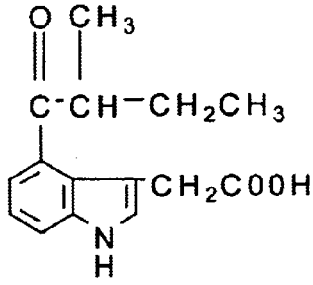
Figure 5:
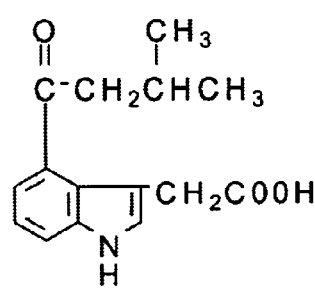
Figure 5:
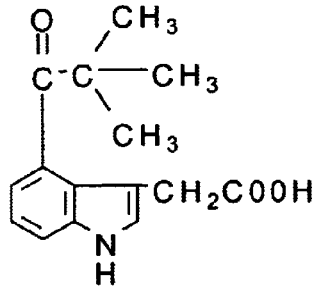
Figure 5:
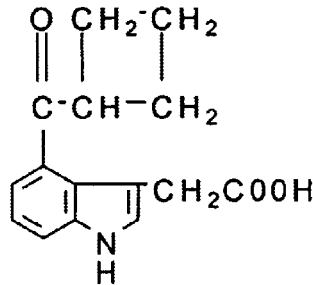

In another embodiment of mono-substituted IAA analogues, acyl substituted IAA compounds are chemically synthesized and tested for plant growth regulatory activity. Shown in FIG. 5 are nine monosubstituted IAA compounds having an acyl substituent group at position 4. The present invention also contemplated acyl-IAA compounds having acyl substituents with 1–10 carbon atoms and having the same or different acyl substituent groups at position 2, 5, 6 or 7. The biological activity of each compound is compared to that of IAA. Different concentrations of each compound are tested for the ability to stimulate root, shoot and callus formation from tobacco and tomato leaf discs and potato stems. The ability to stimulate root formation is evaluated for each compound in the presence of different concentration ratios of cytokinin (e.g., BAP) to test compound.

Figure 6:
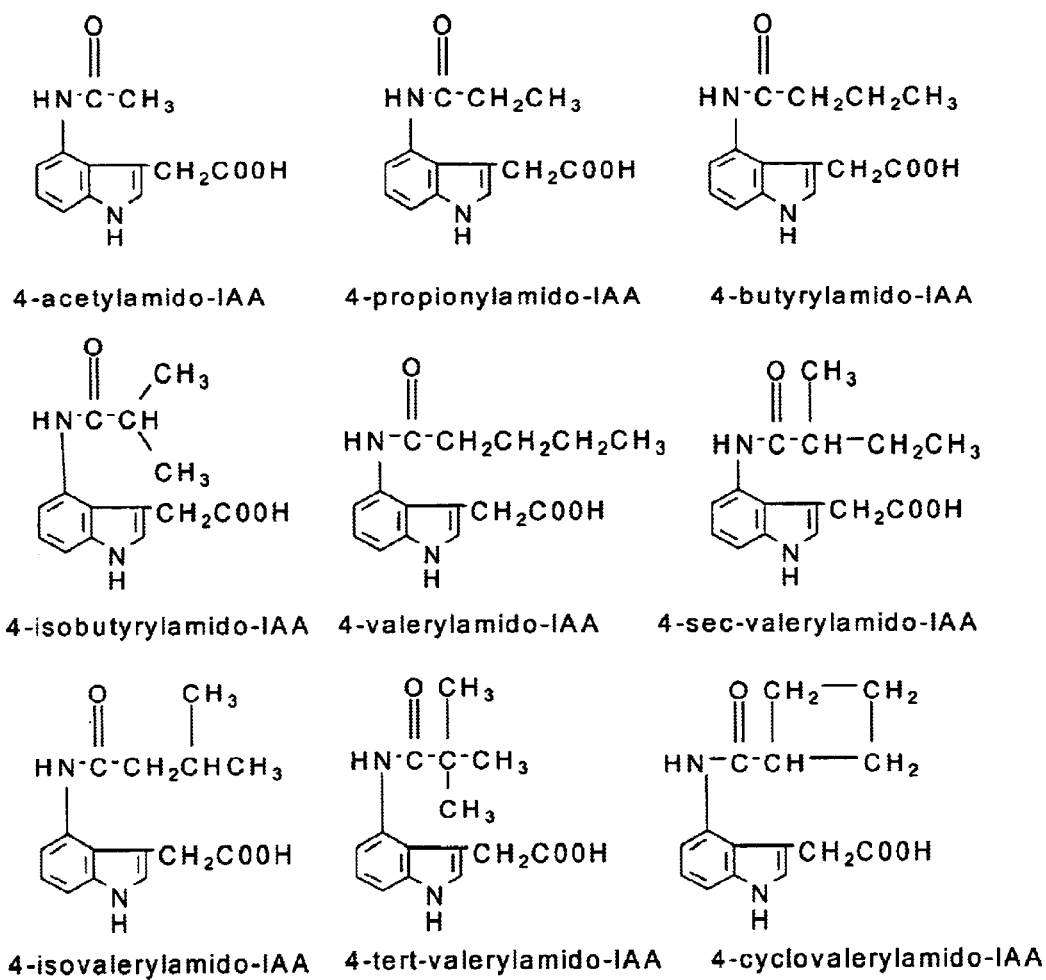
FIG. 6 presents the chemical structures of some monosubstituted, acylamido-IAA auxinic analogues having an acylamido group in the 4 position. The present invention also contemplates acylamido-IAA compounds having the same acylamido substituent group at position 2, 5, 6 or 7. Exemplified in FIG. 6 are acylamido-IAA structures having an acylamido group with 1–4 carbon atoms. The instant invention, however, provides acylamido-substituted IAA molecules having acylamide groups with 1–10 carbon atoms.

In another embodiment of mono-substituted IAA analogues, acylamido substituted IAA compounds are chemically synthesized and tested for plant growth regulatory activity. Shown in FIG. 6 are nine monosubstituted IAA compounds having an acylamido substituent group at position 4. The present invention also contemplated acylamido-IAA compounds having acylamido substituents with 1–10 carbon atoms and having the same acylamido substituent groups at position 2, 5, 6 or 7. The biological activity of each compound is compared to that of IAA. Different concentrations of each compound are tested for the ability to stimulate root, shoot and callus formation from tobacco and tomato leaf discs and potato stems. The ability to stimulate root formation is evaluated for each compound in the presence of different concentration ratios of cytokinin (e.g., BAP) to test compound.

Figure 7:
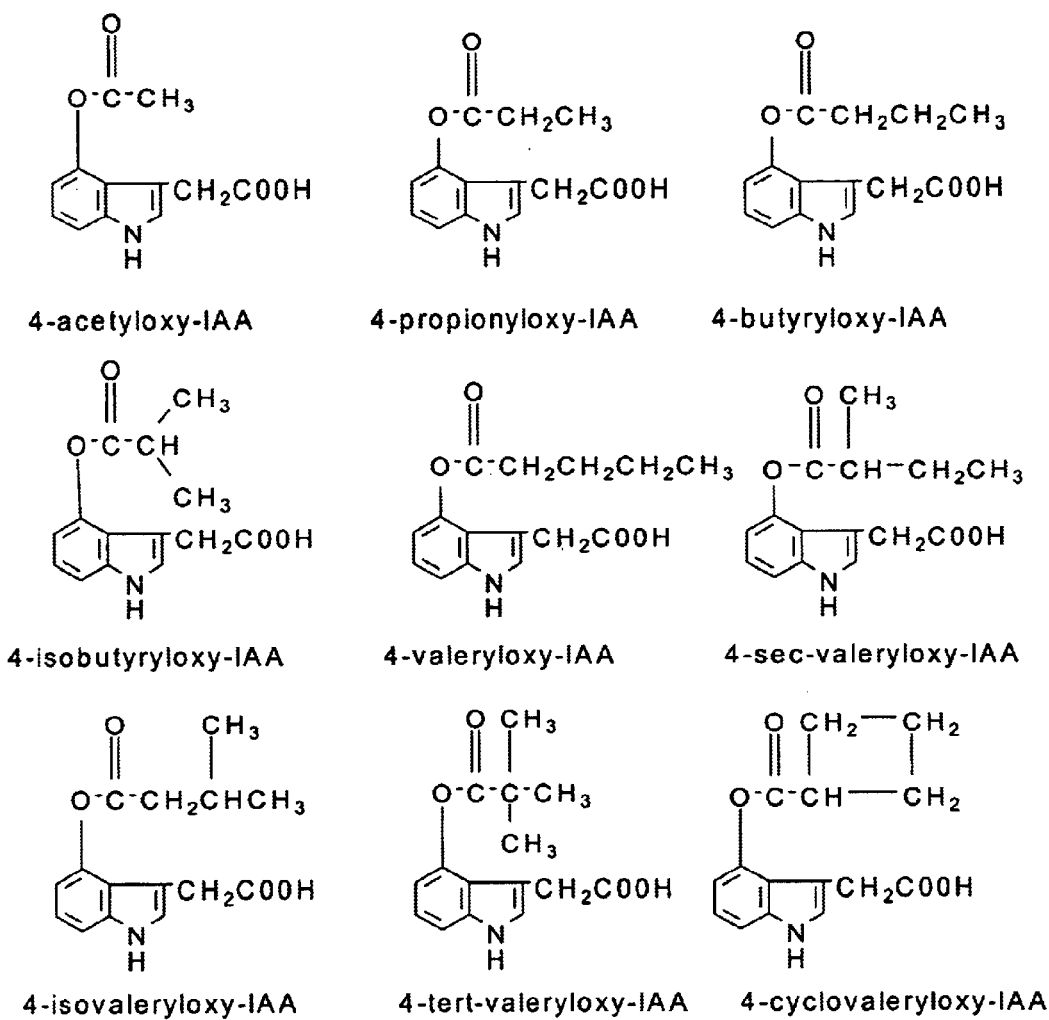
FIG. 7 presents the chemical structures of some monosubstituted, acyloxy-IAA auxinic analogues having an acyloxy group in the 4 position. The present invention also contemplates acyloxy-IAA compounds having the same acyloxy substituent group at position 2, 5, 6 or 7. Exemplified in FIG. 7 are acyloxy-IAA structures having an acyloxy group with 1–4 carbon atoms. The instant invention, however, provides acyloxy substituted IAA molecules having acyloxy groups with 1–10 carbon atoms.

In another embodiment of mono-substituted IAA analogues, acyloxy substituted IAA compounds are chemically synthesized and tested for plant growth regulatory activity. Shown in FIG. 7 are nine monosubstituted IAA compounds having an acyloxy substituent group at position 4. The present invention also contemplated acyloxy-IAA compounds having acyloxy substituents with 1–10 carbon atoms and have the same or different acyloxy substituent groups at position 2, 5, 6 or 7. The biological activity of each compound is compared to that of IAA. Different concentrations of each compound are tested for the ability to stimulate root, shoot and callus formation from tobacco and tomato leaf discs and potato stems. The ability to stimulate root formation is evaluated for each compound in the presence of different concentration ratios of cytokinin (e.g., BAP) to test compound.

In particular embodiments of multi-substituted IAA analogues, di-, tri-, tetra- or penta-substituted IAA compounds, comprising between two and five substituent groups that are individually selected from the group consisting of a halo-, an alkyl-, an alkoxy-, an acyl-, an acylamido- and an acyloxy-substituent group in at least two of the positions corresponding to the 2, 4, 5, 6 or 7 position in the IAA chemical structure of FIG. 1, are synthesized and tested for plant growth regulatory activity. In these multi-substituted IAA compounds, a halo-substituent group includes, but is not limited to, an iodo-, a bromo-, a fluoro- and a chloro-group; an alkyl-substituent group includes, but is not limited to, a linear, branched or cyclic alkyl group, R, having 1–10 carbon atoms; an alkoxy-substituent includes, but is not limited to, a linear, branched or cyclic alkoxy group, RO—, having 1–10 carbon atoms; an acyl-substituent group includes, but is not limited to, a linear, branched or cyclic acyl group, R—C(O)—, having 1–10 carbon atoms; an acylamido-substituent group includes, but is not limited to, a linear, branched or cyclic acylamido-group, R—C(O)—NH—, having 1–10 carbon atoms; and an acyloxy-substituent group includes, but is not limited to, a linear, branched or cyclic acyloxy-group, R—C(O)—O—, having 1–10 carbon atoms.

For each multi-substituted IAA, its auxinic activity is tested and compared to that of IAA. Different concentrations of each compound are tested for the ability to stimulate root, shoot and callus formation from tobacco and tomato leaf discs and potato stems. The ability to stimulate root formation is evaluated for each compound in the presence of different concentration ratios of cytokinin (e.g., BAP) to test compound.

Example 3
The Use of IAA Auxinic Analogues for Stimulating the Regeneration of Transgenic Plants (a) Tobacco Plant transformation is carried out according to the Agrobacterium-mediated transformation procedure essentially as described by Lin et al. [(1994) Focus 16:72–77)].

For tobacco, the leaf discs are incubated with $10^{10}$ cells/ml *Agrobacterium tumefaciens* LBA4404 cells, containing pBI121 harboring the GUS reporter gene, in MS complete medium with 0.5 mg/l 2-(N-morpholino)ethanesulfonic acid (MES) for 10 min, transferred to solid MS complete medium, and incubated for 2 days at 25° C., using an 18 h light/6 h dark cycle for cocultivation. After cocultivation, the explants are transferred to MS media containing different ratios of BAP/IAA or BAP/IAA analogue, 100 mg/l kanamycin and 500 mg/l carbenicillin and incubated at 25° C. using an 18 h light/6 h dark cycle for shoot formation.

(b) Tomato

Plant transformation is carried out according to the *Agrobacterium*-mediated transformation procedure essentially as described by Lin et al. (1994) Focus 16:72–77. Incubation conditions are as described above in section (a) for tobacco.

(c) Potato

Plant transformation in potato stems is carried out as described above in section (a) for tobacco.

(d) *Arabidopsis thaliana*

For *Arabidopsis thaliana*, tissues of hypocotyl are removed from 10-day-old seedlings and preincubated in MS complete medium containing 0.5 mg/l 2,4-D and 0.5 mg/l kinetin for three days. The explants are immersed in $10^9$ cells/ml of *Agrobacterium tumefaciens* LBA4404 containing pBI121 for 20 min, and transferred to solid MS medium containing 500 mg/l carbenicillin, 50 mg/l kanamycin, and various ratios of IAA analogue/2iP or IAA/2iP for callus and shoot formation. *Arabidopsis* explants were incubated at 25° C., using an 18 h light/6 h dark cycle.

(e) Rice.

The transformation of monocotyledonous plants is carried out according to art-known methods as described by Wu, "Methods for Transforming Plant Cells," in *Plant Biotechnology* (1989), Kung and Arntzen, Eds., Butterworth Publishers, Stoneham, Mass. It is preferred that transformation of monocots such as rice and wheat be performed by the particle bombardment method as described in Wang et al. (1988) Plant Mol. Biol. 11:433–439. The regeneration of transformed monocots is performed according to known procedures (Vasil, Biotechnology (1988) 5:387–402) as described in Example 5.

For example, rice (*Oryza sativa*) is transformed using the particle bombardment method of Wang et al. (supra) or the Agrobacterium-mediating technique of Hiel et al. (1994) Plant Journal 6:271 or, alternatively, using the electroporation method as described by Dekeyser et al. (1990) Plant Cell 2:591–602. Regeneration of transformed rice is performed according to Abdullah et al. (1986) Bio/Technology 4:1087–1909 or, alternatively, according to Raineri et al. (1990) Bio/Technology 8:33–38.

In a further example, maize is transformed and regenerated according to the procedures of Rhodes et al. (1988) Bio/Technology 6:56–60 and (1988) Science 240:204–207.

In all cases, an IAA auxinic analogue is used as the auxin to stimulate plant growth in accordance with the invention.

Where required, one or more additional plant growth regulators may be added to the IAA analogue-comprising plant growth compositions.

(f) Cassava.

Stems or leaves preferably the first, second or third leaf, and more preferably the bottom quarter of the leaf closest to the petiole) from one-month-old cassava plants were cut into small pieces. Foreign DNA was inserted by techniques known in the art, e.g., *A. tumifaciens* technique [Lin et al. (1994) supra] or with the microbombardment technique [Schopke et al. (1996) Nature Biotechnology 14:731]. Transgenic cassava tissue was exposed to IAA analogues of the invention and examined for regeneration of cassava tissues.

Figure 10:
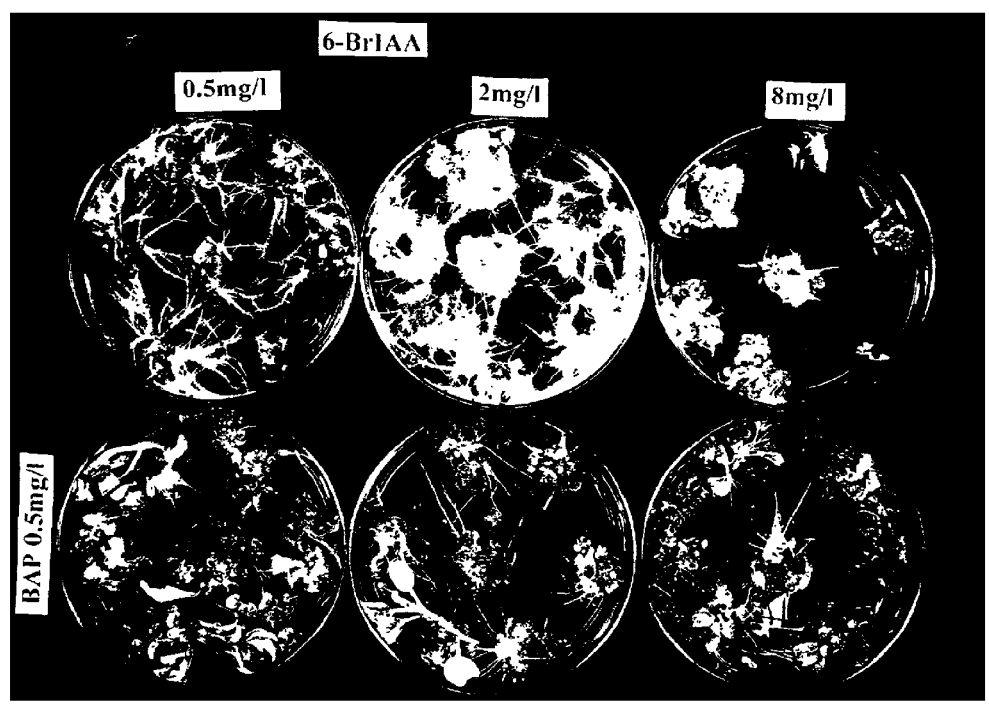
FIG. 10 documents tobacco plant growth with increasing concentrations of 6-BrIAA (0.5, 2.0 and 8.0 mg/l) in the absence (top row) and in the presence (bottom row) of BAP (0.5 mg/l) on the formation of roots and calli (top row) and shoots and calli (bottom row).

Example 4
Screening of Substituted IAA Compounds for Auxinic Activity (a) Non-Transgenic Plants as documented in FIGS. 8–10 and Tables 1, 2 and 4.

Seeds of *Nicotiana tobaccum* Xanthi, potato and tomato were kindly provided by Dr. James Saunders (USDA, Beltsville). Cassava plants were provided by Dr. Dick Sayer (The Ohio State University, Columbus, Ohio).

Young tobacco leaves, potato stems, tomato leaves and cassava leaves and stems from one-month-old plants were removed and cut into small pieces. The explants were incubated on (1) the MS complete medium containing different concentrations of auxin related compounds only (2) the MS complete medium containing different concentrations of auxin-related compounds and 0.5 mg/l benzylaminopurine (BAP) using an 18 hour light/6 hour dark cycle until the formation of green calli, shoots or roots.

The results of root, shoot and callus formations were shown in tomato (FIG. 8), potato (FIG. 9) and tobacco (FIG. 10) and cassava (FIG. 11) incubated in MS complete medium comprising 6-BrIAA only or 6-BrIAA with BAP. The results of screening different IAA analogues for auxinic activities were presented in Table 1 for MS complete medium with IAA analogue only, in Table 2 for MS complete medium with IAA analogue and BAP, and in Table 4 for regeneration of cassava in MS complete medium with different IAA analogues and BAP.

(b) Transgenic Plants as Documented in Table 3.

*Agrobacterium*-mediated plant transformation was performed as described by Lin et al. (1994) Focus 16:72–77. For example:

(i) Tobacco

In tobacco, the leaf discs were incubated with $10^9$ cells/ml of *Agrobacterium tumefaciens* LBA4404 cells containing pBI121 in MS complete medium with 0.5 mg/l MES for 10 minutes, transferred to solid MS complete medium, and incubated for two days at 25° C., using an 18 hour light/6 hour dark cycle for cocultivation. After cocultivation, the explants were transferred to the MS medium containing a different ratio of BAP/IAA or BAP/IAA analogue, 100 mg/l kanamycin and 500 mg/l carbenicillin and incubated at 25° C. using an 18 hour light/6 hour dark cycle for shoot formation.

(ii) Potato

In another example, potato leaf discs were transformed with the Agrobacterium-mediation technique as described above for tobacco. The potato explants were then subjected to incubation with IAA analogues in the absence and presence of cytokinin to screen for auxinic activities.

(iii) Cassava

Stems or third young leaves were removed from the one-month-old Cassava plants and cut into small pieces. The explants were incubated with $10^{10}$ A. tumefaciens cells containing pBI121 for 20 minutes in MS complete liquid medium, transferred to MS complete solid medium and incubated for two days. After two days' incubation, the explants were transferred to MS complete medium with 500 mg/l carbenicillin, 50 mg/l kanamycin, 0.5 mg/l BAP, and different concentrations of auxin related compounds. The explants were incubated at 23° C. using an 18 hour light/six hour dark cycle until the formation of green calli and shoots.

Example 5

Alleviation of Stress with Auxin and Auxin Derivatives (a) Attenuation of Chemical Toxicity.

Figure 12:
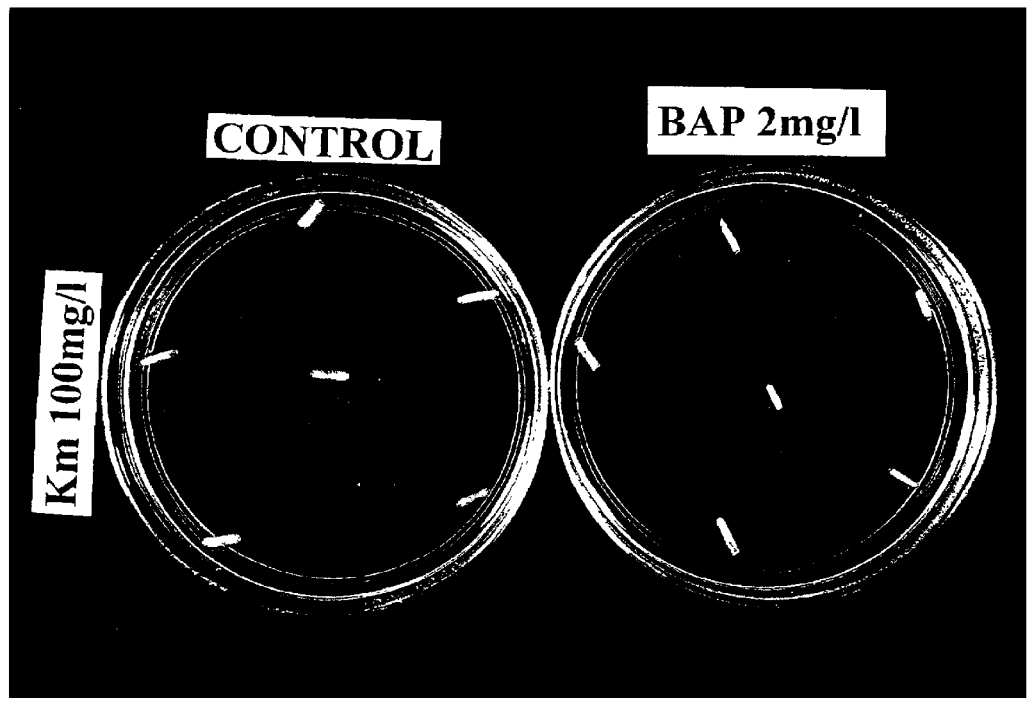
FIG. 12 shows expansion of potato stems incubated in the MS medium containing 2 mg/l NAA and 100 mg/kanamycin.
Figure 12:
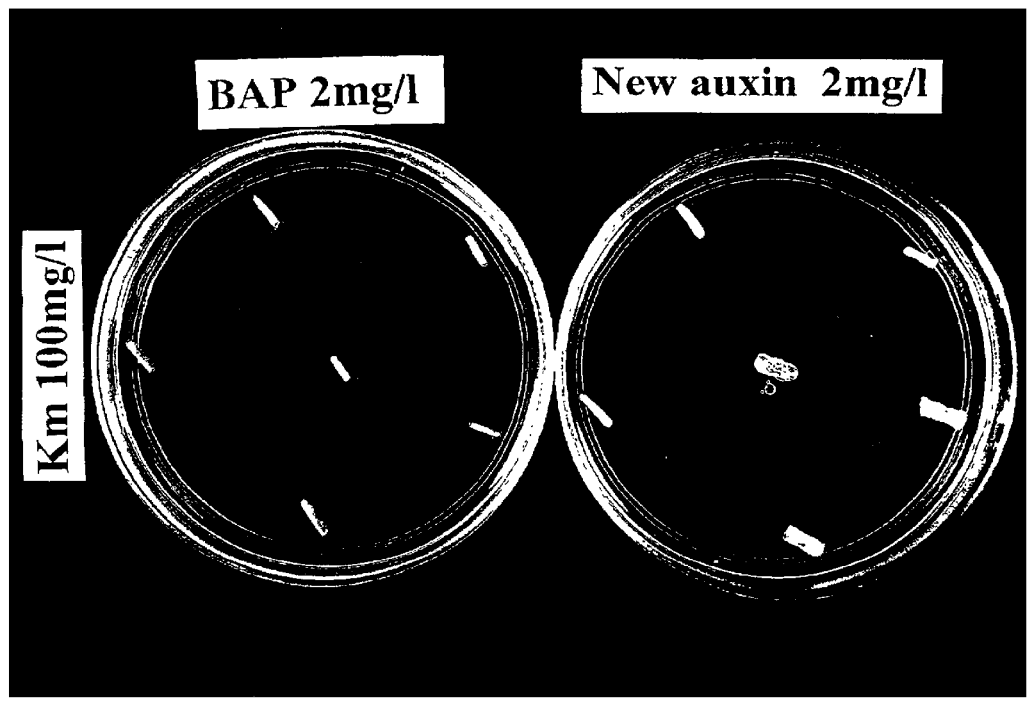
Figure 12:

Potato stems were excised as described above and incubated in the MS complete medium (a) with 25, 50 and 100 mg/l kanamycin and either with/without 2 mg NAA or auxin derivatives or with/without 0.5 mg/l BAP (a ctyokinin). After one month incubation, potato stems incubated in 50 mg or 100 mg/l kanamycin with/without BAP only showed necrosis of stem which indicted the toxicity of kanamycin. However, potato stems incubated in the MS medium containing 2 mg/l NAA and 100 mg/kanamycin, became expanded (FIG. 12). In some cases, the presence of auxin or auxin derivatives showed the formation of calli in some of the potato stems.

Figure 13:
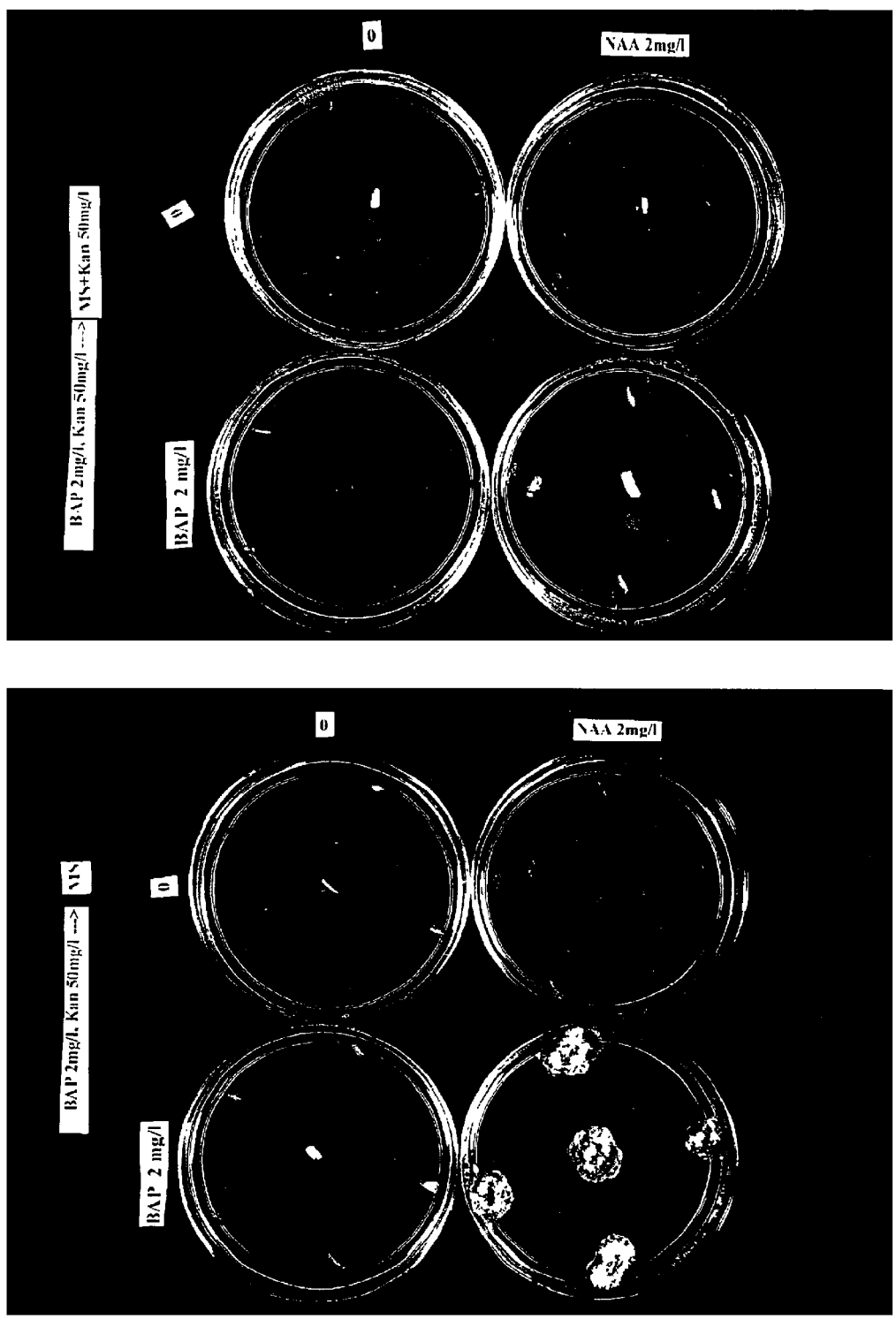
FIG. 13 shows potato stems incubated for one month with kanamycin and BAP and then transferred. All the potato stems were dead after continued incubation without the addition of auxin or auxin derivatives.

In order to confirm that the auxin has the ability to restore the viability of antibiotic treated potato stems, the stems incubated for one month with 50 mg/l kanamycin and 0.5 mg/l BAP were transferred into MS complete medium containing 2 mg/l NAA with/without 100 mg/l kanamycin, or MS medium containing 2 mg/l NAA, 0.5 mg/l BAP, and with/without 100 mg/l kanamycin. The formation of calli on the potato stems was observed when the potato stems were transferred to the MS medium containing auxin or auxin derivative with/without BAP. However, all the potato stems were dead after continued incubation without the addition of auxin or auxin derivatives (FIG. 13).

Similar antibiotics and auxin interactions were observed in the medium containing 2, 4-D, 5-bromo-IAA and IAA. In addition, different antibiotics such as hygromycin and chloramphenicol showed the same interactions with auxin treated potato stems and tobacco leaves.

B. Alleviation of Physical Damage with Auxin and Auxin Derivatives

Tobacco leaves were removed from one month old plants and cut into small pieces (0.5 cm×0.25 cm). These tissues were incubated in the MS complete medium in 0.5 mg/l BAP overnight and bombarded with microprojectiles (1300 psi) (helium source, obtained from BioRad). After bombardment, the tobacco explants were incubated in (1) MS complete medium with 0.5 mg/l BAP, and (2) MS complete medium with 0.5 mg/l BAP and 2 mg/l NAA for three days before transferring to MS complete medium with 0.5 mg/l BAP. Significant improvement of the regeneration of tobacco shoots were shown in those explants incubated in MS medium containing NAA and BAP compared to those shoots incubated in MS medium with BAP only. Moreover, similar results were shown when the tobacco explants were bombarded with pBI121 and incubated with 0.5 mg/l BAP and with/without 2 mg NAA. The transformed tissues were selected by incubation of the explants in MS complete medium with 0.5 mg/l BAP and 100 mg/l kanamycin. All these results demonstrated that auxin were able to alleviate the physical stress such as bombardment and restore the regeneration of plant tissues.

All publications, patent applications and patents cited herein are incorporated by reference in the same extent as if each individual publication, patent application or patent was specifically and individually indicated to be incorporated by reference.

We claim:

1. A method for regeneration of a plant from a plant cell or plant tissue which comprises the steps of:
   (a) contacting said plant cell or plant tissue with an amount of an auxinic compound effective for regeneration of roots and
   (b) contacting said plant cell or plant tissue with a combination of said auxinic compound and a cytokinin in a combined amount effective for the regeneration of shoots from said plant cell or plant tissue wherein said auxinic compound has the formula:

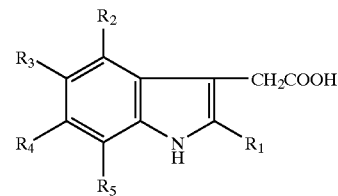

or salts, esters and amides thereof, wherein $R_1$–$R_5$ are independently selected from the group consisting of a hydrogen, a halogen, an alkyl-group, an alkoxy-group, an acyl-group, an acyloxy-group, and an acylamido-group, but excluding indole-3-acetic acid and 5-bromoindole-3-acetic acid.

2. The method of claim 1 wherein said auxinic compound is a monosubstituted indole-3-acetic acid or salt, ester or amide thereof.

3. The method of claim 1 wherein said auxinic compound is a disubstituted indole-3-acetic acid.

4. The method of claim 1 wherein said auxinic compound is 2-fluoroindole-3-acetic acid, 4-fluoroindole-3-acetic acid, 6-fluoroindole-3-acetic acid, 7-fluoroindole-3-acetic acid, 2-bromoindole-3-acetic acid, 4-bromoindole-3-acetic acid, 6-bromoindole-3-acetic acid, 7-bromoindole-3-acetic acid, 2-iodoindole-3-acetic acid, 4-iodoindole-3-acetic acid, 5-iodoindole-3-acetic acid, 6-iodoindole-3-acetic acid, 7-iodoindole-3-acetic acid or salts, esters or abides thereof.

5. The method of claim 1 wherein said auxinic compound is 2-fluoroindole-3-acetic acid, 4-fluoroindole-3-acetic acid, 6-fluoroindole-3-acetic acid, 7-fluoroindole-3-acetic acid or salts, esters or amides thereof.

6. The method of claim 1 wherein said auxinic compound is 6-fluoroindole-3-acetic acid, 7-fluoroindole-3-acetic acid or salts, esters or amides thereof.

7. The method of claim 1 wherein said auxinic compound is 2-bromoindole-3-acetic acid, 4-bromoindole-3-acetic acid, 6-bromoindole-3-acetic acid, 7-bromoindole-3-acetic acid or salts, esters or amides thereof.

8. The method of claim 1 wherein said auxinic compound is 4-bromoindole-3-acetic acid, 6-bromoindole-3-acetic acid, 7-bromoindole-3-acetic acid or salts, esters or amides thereof.

9. The method of claim 1 wherein said auxinic compound is 6-bromoindole-3-acetic acid, 7-bromoindole-3-acetic acid or salts, esters or amides thereof.

10. The method of claim 1 wherein said auxinic compound is 2-iodoindole-3-acetic acid, 4-iodoindole-3-acetic acid, 5-iodoindole-3-acetic acid, 6-iodoindole-3-acetic acid, 7-iodoindole-3-acetic acid or salts, esters or amides thereof.

11. The method of claim 1 wherein in said auxinic compound one of $R_1$–$R_5$ is an alkyl-group and the remaining $R_1$–$R_5$ groups are hydrogens.

12. The method of claim 1 wherein in said auxinic compound one of $R_1$–$R_5$ is an alkoxy-group and the remaining $R_1$–$R_5$ groups are hydrogens.

13. The method of claim 1 wherein said plant cell or tissue is that of a hard-to-regenerate plant.

14. The method of claim 1 wherein said alkyl-group, said alkoxy-group, said acyl-group, said acyloxy-group and said acylamino-group have 1–10 carbon atoms.

15. The method of claim 1 wherein in said auxinic compound at least one of $R_1$–$R_5$ is a halogen.

16. The method of claim 1 wherein said auxinic compound is 2-fluoroindole-3-acetic acid, 4-fluoroindole-3-acetic acid, 6-fluoroindole-3-acetic acid, 7-fluoroindole-3-acetic acid, 2-bromoindole-3-acetic acid, 4-bromoindole-3-acetic acid, 6-bromoindole-3-acetic acid, 7-bromoindole-3-acetic acid, 2-iodoindole-3-acetic acid, 4-iodoindole-3-acetic acid, 5-iodoindole-3-acetic acid, 6-iodoindole-3-acetic acid, or 7-iodoindole-3-acetic acid.

17. The method of claim 1 wherein in said auxinic compound at least one of $R_1$–$R_5$ is an alkyl group.

18. The method of claim 1 wherein said plant cell or plant tissue comprises foreign DNA.

19. The method of claim 1 wherein said plant cell or tissue is of a plant selected from the group of hard to regenerate plants consisting of cassava, woody plants and monocotyledonous plants.

20. The method of claim 1 wherein the plant is a potato.

21. The method of claim 20 wherein the auxinic compound is 7-ethyl indole-3-acetic acid.

* * * * *